(12) United States Patent
Loke et al.

(10) Patent No.: US 8,187,832 B2
(45) Date of Patent: May 29, 2012

(54) METHOD OF DETECTING AN AMOUNT OF A CHOLINESTERASE INHIBITOR IN A SAMPLE

(75) Inventors: Weng Keong Loke, Singapore (SG); Yong Teng Tan, Singapore (SG); Josefina Seow, Singapore (SG)

(73) Assignee: DSO National Laboratories, Singapore (SG)

( * ) Notice: Subject to any disclaimer, the term of this patent is extended or adjusted under 35 U.S.C. 154(b) by 341 days.

(21) Appl. No.: 12/516,297

(22) PCT Filed: Nov. 26, 2007

(86) PCT No.: PCT/SG2007/000406
§ 371 (c)(1),
(2), (4) Date: Jun. 17, 2009

(87) PCT Pub. No.: WO2008/066495
PCT Pub. Date: May 5, 2008

(65) Prior Publication Data
US 2010/0062455 A1 Mar. 11, 2010

(30) Foreign Application Priority Data
Nov. 27, 2006 (SG) ................ 200608245-7

(51) Int. Cl.
*C12Q 1/46* (2006.01)
(52) U.S. Cl. .................................. 435/20; 435/19
(58) Field of Classification Search .............. 435/20, 435/19
See application file for complete search history.

(56) References Cited

U.S. PATENT DOCUMENTS

| 4,324,858 A * | 4/1982 | Goodson et al. ............ 435/20 |
| 6,406,876 B1 | 6/2002 | Gordon et al. |
| 6,783,989 B1 * | 8/2004 | Zakin ......................... 436/104 |
| 2005/0089926 A1 * | 4/2005 | Taylor et al. ................ 435/7.1 |
| 2006/0073490 A1 * | 4/2006 | LeJeune et al. ............. 435/6 |

FOREIGN PATENT DOCUMENTS

WO  WO 94/05808  * 3/1994

OTHER PUBLICATIONS

Degenhardt C. et al. Improvements of the Fluoride Reactivation Method for the Verification of Nerve Agent Exposure. J of Analytical Toxicology 28(5)364-371, Jul./Aug. 2004.*
van der Schaus M. et al. Retrospective Detection of Exposure to Nerve Agents. Arch Toxicol 78:508-524, 2004.*
Degenhardt C. et al. Improvments of the Fluoride Reactivation Method for the Verification of Nerve Agent Exposure. J of Analytical Toxicology vol. 28, 364-371 Jul./Aug. 2004.*
Degenhardt, et al., Improvements of the Fluoride Reactivation Method for the Verification of Nerve Agent Exposure, *Journal of Analytical Toxicology*, vol. 28 (2008).
Jensen et al., Identification of human plasma cholinesterase variants in 6,688 individuals using biochemical analysis, *Acta Anaethesiologica Scandinavica* vol. 39 (1995).
Schans et al., Retrospective detection of exposure to nerve agents: analysis of phosphofluoridates originating from fluoride-induced reactivation of phosphylated BuChE, *Arch Toxicol* 78:508-524 (2004).
Polhuijs et al., New Method for Retrospective Detection of Exposure to Organophosphorus Anticholinesterases: Application to Alleged Sarin Victims of Japanese Terrorists, *Toxicology and Applied Pharmacology* 146, 156-161 (1997).
Shih et al., Cerebral acetylcholine and choline contents and turnover following low-dose acetylcholinesterase inhibitors treatment in rats, *Arch Toxicol* 80:761-767 (2006).
Degenhardt, C., et al., "Improvements of the Fluoride Reactivation Method for the Verification of Nerve Agent Exposure". Journal of Analytical Toxicology (2004), vol. 28(5): 364-371.
Jensen, F.S., et al. "Identification of human plasma cholinesterase variants in 6,688 individuals using biochemical analysis". Acta Anaesthesiologica Scandinavica (1995), vol. 39(2): 157-162.

* cited by examiner

*Primary Examiner* — Ralph Gitomer

(57) ABSTRACT

A method of detecting an amount of a cholinesterase inhibitor in a sample comprising steps of: (a) contacting the sample with an agent capable of recovering the cholinesterase inhibitor from the sample so that the cholinesterase inhibitor is recovered, wherein the agent comprises a reactivity towards phosphyl moieties; (b) isolating the recovered cholinesterase inhibitor from the sample; (c) contacting the isolated cholinesterase inhibitor from step (b) with a test cholinesterase wherein the cholinesterase activity of the test cholinesterase before step (a) is known; and (d) measuring the cholinesterase activity to determine the amount of cholinesterase inhibitor in the sample based on the inhibition of the test cholinesterase activity from the known activity of the test cholinesterase before step (a).

30 Claims, 18 Drawing Sheets

Figure 5

Regeneration efficiency of spiked 40nM VX in blood with various KF concentrations (15mins ImmAChE inhibition)

Figure 6

%Inhibition of ImmAChE after GB regeneration: Vary pH effects (Volume of acetate buffer with KF)

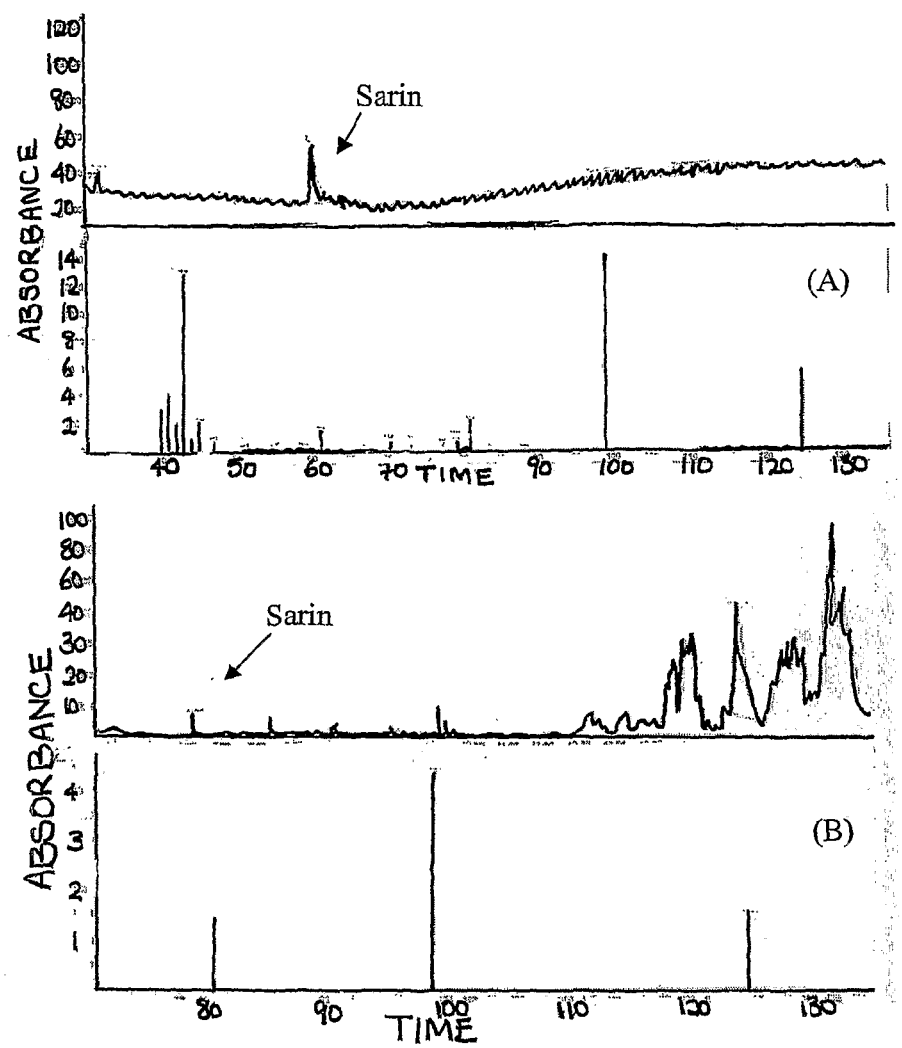
Figure 24 (A) and (B)
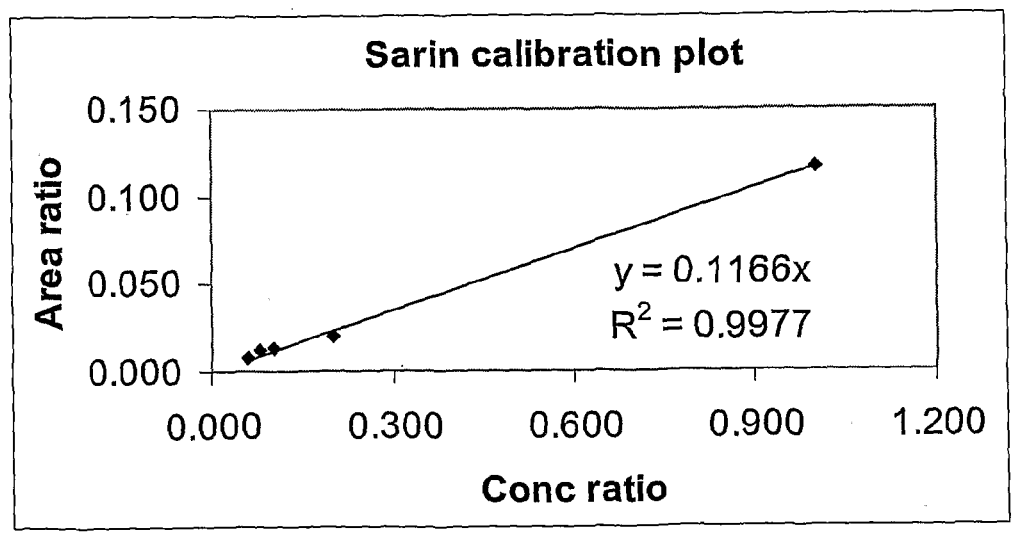
Figure 25

Orientation of tubes in 96-position rack

|   | 1 | 2 | 3 | 4 | 5 | 6 | 7 | 8 | 9 | 10 | 11 | 12 |
|---|---|---|---|---|---|---|---|---|---|----|----|----|
| A | 1 | 9 | 17 | 25 | 33 | 41 | 49 | 57 | 65 | 73 | 81 | 89 |
| B | 2 | 10 | 18 | 26 | 34 | 42 | 50 | 58 | 66 | 74 | 82 | 90 |
| C | 3 | 11 | 19 | 27 | 35 | 43 | 51 | 59 | 67 | 75 | 83 | 91 |
| D | 4 | 12 | 20 | 28 | 36 | 44 | 52 | 60 | 68 | 76 | 84 | 92 |
| E | 5 | 13 | 21 | 29 | 37 | 45 | 53 | 61 | 69 | 77 | 85 | 93 |
| F | 6 | 14 | 22 | 30 | 38 | 46 | 54 | 62 | 70 | 78 | 86 | 94 |
| G | 7 | 15 | 23 | 31 | 39 | 47 | 55 | 63 | 71 | 79 | 87 | 95 |
| H | 8 | 16 | 24 | 32 | 40 | 48 | 56 | 64 | 72 | 80 | 88 | 96 |

Click on Green Cell and paste Pre-Inhibition Read data [Ctrl+V]

|   | 1 | 2 | 3 | 4 | 5 | 6 | 7 | 8 | 9 | 10 | 11 | 12 |
|---|---|---|---|---|---|---|---|---|---|----|----|----|
| A | 168.6 | 170.8 | 170.3 | 183.2 | 171.4 | 159.8 | 164.2 | 151.5 | 150.7 | 132.8 | 135.2 | 166.4 |
| B | 149.2 | 152.6 | 158.8 | 182.6 | 168.4 | 155.3 | 149.6 | 139.5 | 143.4 | 136.8 | 131.9 | 157.4 |
| C | 138.9 | 135.0 | 149.5 | 178.3 | 169.2 | 162.6 | 147.6 | 137.3 | 143.3 | 148.9 | 143.3 | 165.7 |
| D | 138.5 | 138.4 | 139.7 | 162.5 | 171.6 | 165.0 | 125.5 | 132.8 | 137.9 | 146.3 | 149.4 | 150.0 |
| E | 152.8 | 137.2 | 136.5 | 155.6 | 169.7 | 156.4 | 138.9 | 140.0 | 132.0 | 134.6 | 153.9 | 152.7 |
| F | 153.2 | 144.1 | 140.8 | 155.8 | 158.9 | 146.9 | 130.3 | 144.9 | 128.4 | 144.7 | 147.3 | 156.9 |
| G | 150.4 | 151.4 | 154.2 | 146.9 | 144.1 | 144.2 | 122.3 | 146.4 | 131.1 | 149.6 | 135.6 | 156.0 |
| H | 158.5 | 162.8 | 162.9 | 171.3 | 155.9 | 152.1 | 145.0 | 163.4 | 146.4 | 147.4 | 148.3 | 161.6 |

Click on Red Cell and paste Post-Inhibition Read data [Ctrl+V]

|   | 1 | 2 | 3 | 4 | 5 | 6 | 7 | 8 | 9 | 10 | 11 | 12 |
|---|---|---|---|---|---|---|---|---|---|----|----|----|
| A |   | 149.4 | 159.5 | 171.7 | 162.6 | 164.1 | 161.4 | 168.5 | 124.8 | 149.3 | 158.9 | 164.1 |
| B | 65.7 | 147.5 | 160.9 | 169.4 | 162.2 | 162.1 | 153.3 | 158.2 | 167.6 | 160.4 | 120.0 | 156.6 |
| C | 67.8 | 150.1 | 165.4 | 179.2 | 161.9 | 166.3 | 158.1 | 154.4 | 168.7 | 168.2 | 132.7 | 187.7 |
| D | 67.9 | 153.3 | 157.5 | 184.3 | 172.4 | 173.5 | 139.0 | 151.6 | 163.5 | 171.1 | 133.9 | 146.2 |
| E | 77.9 | 155.3 | 157.7 | 176.6 | 178.8 | 94.8 | 156.7 | 170.0 | 159.4 | 168.2 | 140.5 | 155.8 |
| F | 160.2 | 150.6 | 155.8 | 166.0 | 182.4 | 92.5 | 152.2 | 172.6 | 160.6 | 179.6 | 175.7 | 165.5 |
| G | 157.4 | 156.3 | 160.9 | 153.0 | 171.7 | 92.6 | 159.3 | 181.1 | 163.2 | 186.0 | 159.2 | 159.3 |
| H | 170.4 | 170.9 | 173.6 | 177.8 | 184.8 | 89.7 | 169.1 | 186.8 | 165.4 | 166.0 | 163.6 | 172.5 |

Results

|   | 1 | 2 | 3 | 4 | 5 | 6 | 7 | 8 | 9 | 10 | 11 | 12 |
|---|---|---|---|---|---|---|---|---|---|----|----|----|
| A | OK | OK | OK | OK | OK | OK | OK | OK | OK | OK | OK | OK |
| B | X | OK | OK | OK | OK | OK | OK | OK | OK | OK | OK | OK |
| C | X | OK | OK | OK | OK | OK | OK | OK | OK | OK | OK | OK |
| D | X | OK | OK | OK | OK | OK | OK | OK | OK | OK | OK | OK |
| E | X | OK | OK | OK | OK | X | OK | OK | OK | OK | OK | OK |
| F | OK | OK | OK | OK | OK | X | OK | OK | OK | OK | OK | OK |
| G | OK | OK | OK | OK | OK | X | OK | OK | OK | OK | OK | OK |
| H | OK | OK | OK | OK | OK | X | OK | OK | OK | OK | OK | OK |

Legend

| Meaning | Symbols |
|---|---|
| No exposure to nerve agent | OK |
| Exposure to nerve agent | X |
| Unable to curve fit (refer to kinetic plot) | ? |
| Unable to curve fit in kinetic plot : | *** |

Figure 30

| Position | Tube# | Name | NRIC | Results | |
|---|---|---|---|---|---|
| A1 | 1 | | | OK | |
| B1 | 2 | | | X | Exposed! |
| C1 | 3 | | | X | Exposed! |
| D1 | 4 | | | X | Exposed! |
| E1 | 5 | | | X | Exposed! |
| F1 | 6 | | | OK | |
| G1 | 7 | | | OK | |
| H1 | 8 | | | OK | |
| A2 | 9 | | | OK | |
| B2 | 10 | | | OK | |
| C2 | 11 | | | OK | |
| D2 | 12 | | | OK | |
| E2 | 13 | | | OK | |
| F2 | 14 | | | OK | |
| G2 | 15 | | | OK | |
| H2 | 16 | | | OK | |
| A3 | 17 | | | OK | |
| B3 | 18 | | | OK | |
| C3 | 19 | | | OK | |
| D3 | 20 | | | OK | |
| E3 | 21 | | | OK | |
| F3 | 22 | | | OK | |
| G3 | 23 | | | OK | |
| H3 | 24 | | | OK | |
| A4 | 25 | | | OK | |
| B4 | 26 | | | OK | |
| C4 | 27 | | | OK | |
| D4 | 28 | | | OK | |
| E4 | 29 | | | OK | |
| F4 | 30 | | | OK | |
| G4 | 31 | | | OK | |
| H4 | 32 | | | OK | |
| A5 | 33 | | | OK | |
| B5 | 34 | | | OK | |
| C5 | 35 | | | OK | |
| D5 | 36 | | | OK | |
| E5 | 37 | | | OK | |
| F5 | 38 | | | OK | |
| G5 | 39 | | | OK | |
| H5 | 40 | | | OK | |
| A6 | 41 | | | OK | |
| B6 | 42 | | | OK | |
| C6 | 43 | | | OK | |
| D6 | 44 | | | OK | |
| E6 | 45 | | | X | Exposed! |
| F6 | 46 | | | X | Exposed! |
| G6 | 47 | | | X | Exposed! |
| H6 | 48 | | | X | Exposed! |
| A7 | 49 | | | OK | |
| B7 | 50 | | | OK | |
| C7 | 51 | | | OK | |
| D7 | 52 | | | OK | |
| E7 | 53 | | | OK | |
| F7 | 54 | | | OK | |
| G7 | 55 | | | OK | |
| H7 | 56 | | | OK | |
| A8 | 57 | | | OK | |
| B8 | 58 | | | OK | |
| C8 | 59 | | | OK | |
| D8 | 60 | | | OK | |
| E8 | 61 | | | OK | |
| F8 | 62 | | | OK | |
| G8 | 63 | | | OK | |
| H8 | 64 | | | OK | |
| A9 | 65 | | | OK | |
| B9 | 66 | | | OK | |
| C9 | 67 | | | OK | |
| D9 | 68 | | | OK | |
| E9 | 69 | | | OK | |
| F9 | 70 | | | OK | |
| G9 | 71 | | | OK | |
| H9 | 72 | | | OK | |
| A10 | 73 | | | OK | |
| B10 | 74 | | | OK | |
| C10 | 75 | | | OK | |
| D10 | 76 | | | OK | |
| E10 | 77 | | | OK | |
| F10 | 78 | | | OK | |
| G10 | 79 | | | OK | |
| H10 | 80 | | | OK | |
| A11 | 81 | | | OK | |
| B11 | 82 | | | OK | |
| C11 | 83 | | | OK | |
| D11 | 84 | | | OK | |
| E11 | 85 | | | OK | |
| F11 | 86 | | | OK | |
| G11 | 87 | | | OK | |
| H11 | 88 | | | OK | |
| A12 | 89 | | | OK | |
| B12 | 90 | | | OK | |
| C12 | 91 | | | OK | |
| D12 | 92 | | | OK | |
| E12 | 93 | | | OK | |
| F12 | 94 | | | OK | |
| G12 | 95 | | | OK | |
| H12 | 96 | | | OK | |

Figure 31

METHOD OF DETECTING AN AMOUNT OF A CHOLINESTERASE INHIBITOR IN A SAMPLE

PRIORITY CLAIM

This is a U.S. national stage of PCT Application No. PCT/SG2007/000406, filed on Nov. 26, 2007, claiming priority from Singapore Application No. 200608245-7, filed: Nov. 27, 2006, the contents of all of which are incorporated here by reference.

FIELD OF THE INVENTION

The invention relates to a rapid method for detection of cholinesterase inhibitors kits for uses thereof and methods of manufacture.

BACKGROUND ART

Cholinesterase is a term which refers to one of the two enzymes: Acetylcholinesterase (AChE), and Pseudocholinesterase (BChE or BuChE), also known as *plasma cholinesterase*, or *butyrylcholinesterase*. Both of these compounds catalyze the hydrolysis of the neurotransmitter acetylcholine into choline and acetic acid, a reaction necessary to allow a cholinergic neuron to return to its resting state after activation.

In 1968, Walo Leuzinger successfully purified and crystallized the enzyme from electric eels at Columbia University, NY. Several cholinesterases are commercially available typically from animal or marine sources such as horse, cow, electric eels and the like. Cholinesterase is relatively instable and is best kept at low temperatures. Some attempts to stabilise the enzyme by immobilizing it on a porous surface or platform as in U.S. Pat. No. 6,406,876 or dehydrating the enzyme so it can be safely stored and later rehydrated for use as in U.S. Pat. No. 4,324,858 have been attempted. In actual use it is, however difficult to obtain a sensitive, simple, portable, economic kit or method for rapid detection of cholinesterase inhibitors without resorting to cumbersome steps for the improvement of shelf life.

A cholinesterase inhibitor (or "anticholinesterase") suppresses the action of the enzyme. Because of its essential function, chemicals that interfere with the action of cholinesterase are potent neurotoxins, causing excessive salivation and eye watering in low doses, followed by muscle spasms, respiratory failure, convulsions and ultimately death. Examples of cholinesterase inhibitors are some snake venoms, organophosphate pesticides, and the nerve gases sarin, Soman, Tabun, Cyclosarin VR and VX.

During the Sarin incident in the Tokyo subway in 1995, an incredible influx of over 600 casualties reported to one of the hospital's Emergency Department within the initial hours of the incident. In all, the hospital's Emergency Department received a total 640 patients, of which an overwhelming 99.2% did not require emergency treatment. 82.5% patients had only mild symptoms and hence could be classified under the category of mass psychogenic illness. Such a huge influx of patients into hospitals following any chemical nerve agent event is likely to be a common aftermath of future terrorist actions and is expected to severely reduce the efficiency of any Emergency Department. An efficient and rapid screening procedure would be required at the hospital triage stage to differentiate those requiring medical attention due to moderate and severe exposure; inclusive of dermal exposure, from amongst the worried-well or psychogenic masses.

As symptoms of chest tightness and headache arising from mass psychogenic reaction cases resemble clinical signs of mild to moderate inhalation exposure to nerve agents, there exists a genuine difficulty in distinguishing such "worried-well" cases from exposed casualties by clinical symptoms alone. The current diagnostic kit for monitoring an individual's exposure to nerve agents/organophosphorous pesticides is by monitoring for a 30% decrement in blood cholinesterase from baseline values. Such kits include EQM Testmate and automated laboratory cholinesterase assays from Walter Reed Army Institute of Research. However, these biomonitoring techniques require prior establishment of the individual's baseline acetylcholinesterase levels, which limits their application in sudden terrorist incidents involving nerve agents or organophosphorus (OP) inhibitors. Moreover, upon administration of pre-treatment medication, pyridostigmine by first responders, inter-individual variance in degree of blood cholinesterase inhibition (10-50% inhibition), complicates efforts to diagnose subsequent exposure to nerve agents using blood cholinesterase measurements. There is hence a paucity of definitive, rapid mass triage diagnostic devices to resolve similar mass casualty problem as encountered during the Tokyo Subway Sarin Attack.

Amongst non-exposed individuals, intra-individual variation in erythrocyte AChE activities could be as much as 13% while that between individuals could range from 75-150% of mean population baseline AChE level. These normal values are so wide that it is possible for patients to have substantial decline in erythrocyte AChE level and yet stay within the population normal range. During organophosphate exposures, appearance of clinical symptoms is also more dependent on the rate of decline in AChE level than on the absolute level of erythrocyte AChE observed. Hence, while most cases manifest clinical symptoms when erythrocyte AChE is inhibited by 70-80%, clinical manifestations have also been recorded at 40-50% erythrocyte AChE inhibition. On the other hand, symptoms may also appear following sudden acute exposure associated with a rapid drop of synaptic AChE even when erythrocyte AChE inhibition is less than 30%. Moreover, as erythrocyte AChE level is also known to be affected by nutritional or water deficiency and pregnancy, a threshold of 30% inhibition of erythrocyte AChE has been selected as a reference level for indicating possible organophosphate exposure. In the absence of clinical symptoms, erythrocyte acetylcholinesterase (AChE) inhibition less than 30% has little utility for confirming OP exposure nor could it rule out possible toxic sequela following exposure. In view of the inherent fluctuations in the level of this natural biomarker, monitoring of erythrocyte AChE level has serious limitations for diagnosis of low-level OP exposure, which may record AChE inhibition less than 30% and little or no clinical signs and symptoms of OP poisoning. Knowing each individual's pre-exposure AChE baseline level would assist in diagnosis of low level OP exposure but this is not feasible in terrorist attack scenarios. The eye's response, on the other hand, while being more responsive than AChE inhibition to OP, is not confirmatory of organophosphate exposure as miosis can also be produced by barbiturate overdose.

One of the most common classes of cholinesterase inhibitors are phosphorus-based compounds which bind to the active site of the enzyme. The structural requirements are a phosphorus atom bearing two lipophilic groups, a leaving group such as a halide or thiocyanate and a terminal oxygen.

Cholinesterase inhibitors are also used in anesthesia or in the treatment of myasthenia gravis, glaucoma and Alzheimer's disease. Also such compounds are used for killing insects in a range of products including sheep dip, organophosphate pesticides, and carbamate pesticides. In addition to acute poisoning as described above, a semi-acute poisoning characterized by strong mental disturbances can occur. Also, prolonged exposure can cause birth defects. The toxic nature of organophosphate, organosulfur and carbamate pesticides has led to several regulatory requirements to protect people who handle such pesticides. This includes monitoring occupational exposure to the pesticide by routinely measuring the blood cholinesterase levels of people handling the pesticides. A current portable diagnostic method available known as the Test-mate system, requires each individual's pre-exposure cholinesterase baseline level. This is not feasible in situations where there were previously no regulations in a particular country or area and an individual has been exposed for many years without having had their pre-exposure baseline cholinesterase level tested.

Generally if someone is suspected of having been exposed to a cholinesterase inhibitor, treatment protocols dictate that treatment should be instituted based on appearance of clinical symptoms and without waiting for test results of laboratory tests. As symptoms of chest tightness and headache arising from mass psychogenic reaction cases resemble clinical signs of mild to moderate inhalation exposure to nerve agents, there is a possibility of inappropriate antidote administration to non-intoxicated patients. The most common treatments include atropine and oximes. Oximes such as pralidoxime and Hagedorn oximes such as obidoxime and HI-6, themselves interfere with cholinesterase levels in the blood through their actions on cholinesterase inhibitors or through direct effects on cholinesterases. This can interfere with conventional measurement of cholinesterase levels in the blood as an indicator of exposure to a cholinesterase inhibitor and prevent retrospective diagnosis post-antidotes administration.

Upon intoxication with organophosphorus (OP) chemicals, these agents bind rapidly to cholinesterases in blood, and hence intact free agents in blood disappear soon after exposure, causing difficulty in detecting the free OP chemicals. However, retrospective analysis is made possible using reactivation method with fluoride ions, as demonstrated in regeneration of these protein-bound nerve agent sarin in blood samples of alleged sarin victims of Tokyo (1995) and Matsumoto (1994) terrorist attacks (Martine Polhuijs, et. al. New Method for Retrospective Detection of Exposure to Organophosphorus Anticholinesterases: Application to blood samples of alleged Sarin Victims of Japanese Terrorists. *Toxicology and Applied Pharmacology* 1997; 146: 156-161). This method focuses on detection of the cholinesterase inhibitor present in a sample rather than the conventional test for cholinesterase level of a sample. However, the method is laboratory bound as it required the use of solid-phase extraction or liquid-liquid extraction and analysis by sophisticated expensive equipment like GC-MS. The technique takes about 20 minute per sample and it would take more than 3 hours to complete 10 samples. It is not suitable for rapid field tests in a terrorist situation and would be a very expensive monitor for occupational exposure to pesticides.

The present invention seeks to provide a rapid method for detection of cholinesterase inhibitors as an indication of exposure to the cholinesterase inhibitor. It provides a kit for carrying out the methods.

General

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

SUMMARY OF THE INVENTION

A first aspect of the invention provides a method of detecting the presence of an amount of cholinesterase inhibitor in a sample comprising the steps of: (a) contacting the sample with an agent capable of recovering any cholinesterase inhibitor in the sample; (b) contacting any cholinesterase inhibitor from step (a) with a cholinesterase wherein the cholinesterase activity is known; and (c) measurement of the cholinesterase activity to determine the inhibition of cholinesterase activity from the known activity.

Advantageously this method determines whether an individual has been exposed to a cholinesterase inhibitor by measuring the actual cholinesterase inhibitor in a sample either free or recovered from a cholinesterase-inhibitor complex to determine if the individual may require further treatment or avoidance of future exposure. The known cholinesterase activity provides an artificial cholinesterase activity independent of an individual's pre-exposure level of cholinesterase. As the detection method detects any cholinesterase inhibitor rather than the level of blood cholinesterase the variation in such blood levels between individuals does not factor into the detection. The method may allow two or more samples to be measured rapidly at the same time.

The method may further comprise the step wherein the agent is removed from the sample before step (b) filtering any free and reactivated cholinesterase inhibitor through an inert hydrophilic filter optionally packed with insoluble aluminium.

A second aspect of the invention provides a kit for detection of a cholinesterase inhibitor in a sample comprising; an agent capable of recovering a cholinesterase inhibitor; and cholinesterase.

A third aspect of the invention provides a method of manufacturing a kit for detection of a cholinesterase inhibitor in a sample comprising; preparing an agent capable of recovering a cholinesterase inhibitor from a sample and preparing a cholinesterase

BRIEF DESCRIPTION OF THE DRAWINGS

FIG. 5: Regeneration of VX Spiked (40 nM) In human blood Samples By Various [KF] Used in Regeneration Buffer FIG. 6: Detection of Cholinesterase inhibitor using a range of varying ratio of acetate buffer volume to blood sample volume.

FIG. 17: Limit of detection (LOD) of the Cholinesterase inhibitor VX at a range of concentrations of cholinesterase inhibitor spiked into blood samples using an exemplary kit.

FIG. 18: Limit of detection (LOD) of the Cholinesterase inhibitor Tabun at a range of concentrations of cholinesterase inhibitor spiked into blood samples using an exemplary kit.

FIG. 24 A & B: GC-MS (EI) Chromatograms of Sarin Standard in Scan Mode (A) and recovered inhibitor in Current test kit Filtrate, in SIM Mode (B). Identity of Recovered Inhibitor is Determined to be Sarin by the selected ions m/z 125, 99 and 81, which are representative of sarin nerve agent.

FIG. 25: Calibration Plot Obtained from GC-MS (EI) Analysis of Various Sarin Standards of A Range of Prepared Concentrations

FIG. 30: An exemplary results template from an exemplary kit for detection of cholinesterase inhibitor.

FIG. 31: An exemplary data entry format, where the results for each individual will appear next to names, as the results data are automatically linked to the template in FIG. 26.

DETAILED DISCLOSURE OF THE INVENTION

Figure 1:
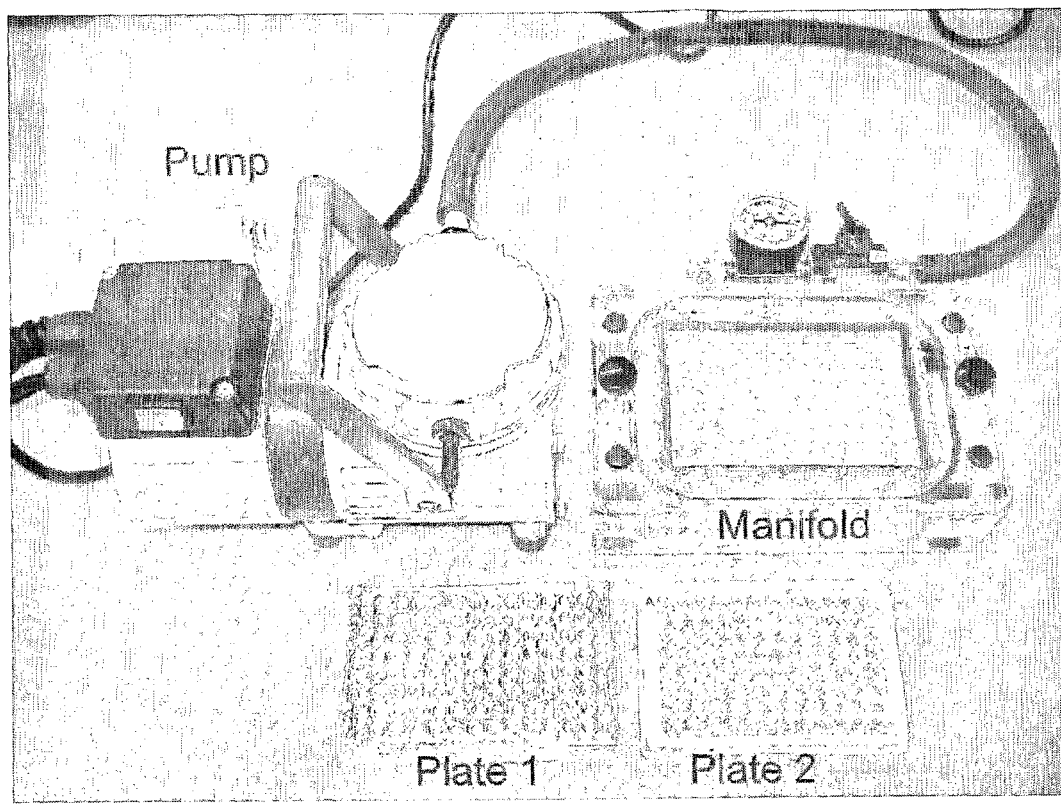
FIG. 1: Exemplary setup of small vacuum pump and vacuum manifold for filter to surface or platform vacuum filtration using 96-well plates.

A first aspect of the invention provides a method of detecting the presence of an amount of cholinesterase inhibitor in a sample comprising the steps of: (a) contacting the sample with an agent capable of recovering any cholinesterase inhibitor in the sample; (b) contacting any reactivated cholinesterase inhibitor from step (a) with a cholinesterase wherein the cholinesterase activity is known; and (c) measurement of the cholinesterase activity to determine the inhibition of cholinesterase activity from the known activity.

A sample may be a biological sample such as a blood, plasma, urine or other body fluid of an individual that may have been exposed to a cholinesterase inhibitor. The volume of the sample could be in the range 1 to 100 µl or more preferably in the range of 15 to 50 µl or 20 to 25 µl or most preferably 20 µl. The sample could be taken from a simple blood test such as a finger prick with a lancet wherein the blood is then removed from the puncture site in a capillary such as a heparinised capillary.

The agent capable of recovering a cholinesterase inhibitor in a sample comprises a reactivity towards phosphyl moieties such an agent may include an active site of an oxime or fluoride ions or molybdite ions, Magnesium ions, Cobalt ions, Nickel ions, Copper salts such as copper sulphates including copper chelates, and the like. Concentrations of fluoride or other ions may be used in the range 1 mM to 2 M. Regenerating a cholinesterase is best done at an acidic pH. Potassium or sodium fluoride (KF or NaF) may be used preferably acidified by an acetate buffer. The volume of acetate buffer with respect to the sample volume is in the range of 2 to 6 or more preferably in the range 3-6.5 or most preferably a volume of 6.5.

The method may further comprise the step (a.1) wherein the agent is removed from the sample before step (b)

A cholinesterase is an enzyme. There are two naturally occurring cholinesterase: Acetylcholinesterase (AChE), and Pseudocholinesterase (BChE or BuChE). There are several cholinesterase enzymes commercially available typically from animal or marine sources such as horse, cow, electric eels, recombinant, other erythrocytes and the like. The cholinesterase used may be from any of these sources including non-human and human sources. The cholinesterase may also be the active peptide component capable of interaction with a cholinesterase inhibitor. The cholinesterase may further be dehydrated as this may increase its shelf life. The cholinesterase may further be immobilized (ImmAChE) on a support as this may increase its shelf life and portability. A protective layer of macromolecules may be placed over the immobilized cholinesterase to enhance its stability in the presence of high humidity.

In a preferred form of the invention the sample if passed through the filter allowed reactivated cholinesterase inhibitor to contact the cholinesterase. Desirably, the filter is an inert hydrophilic type filter to retain blood proteins. The filtration may be left unaided, pumped or vacuum filtered through to the corresponding detection sites. The method further comprises filtering multiple samples simultaneously and preferably 96 samples are filtered simultaneously. The vacuum pump may be used at a pressure of at 10 Hg or more for a duration of about 1 minute.

An inert hydrophilic filter is a filter that is inert or chemically resistant in some cases this may include a small amount of Teflon or gold or other inert substances but not so much that it would reduce the movement of water through the filter. A hydrophilic filter with packed alumina will allow aqueous solutions to pass through without allowing precipitated blood proteins or free agent to pass through. Some examples of an inert hydrophilic filter comprise Nitrocellulose membrane such as those with a 0.45 µm or larger pore size, PolyViNyliDene Fluoride (PVDF) or Polytetrafluoroethylene (PTFE) such as those with a 0.45 µm or larger pore size that are at concentrations that are hydrophilic in nature. The agent is best removed from the sample as it may react with the cholinesterase interfering with detection any activated cholinesterase inhibitor. Fluoride ions can inhibits cholinesterase and inhibition may be increased with lowering of pH. As the activation occurs at an acidic pH it is important to remove the agent such as fluoride ions with an inert hydrophilic filter.

The filter may be packed with insoluble aluminium compounds such as beads conjugated with aluminium or alumina, aluminium oxide and the like. The insoluble aluminium may be in the range of 0.5 to 0.075 g when 20 µl of sample is used or more preferably in the range of 0.5 to 0.075 g or most preferably 0.1 to 0.15 g are used per 20 µl of sample. This may be extrapolated to infer that a range of 0.009 g to 0.0075 g of insoluble aluminium can be used per 1 µl of sample. This may further remove any free agent such as fluoride ions from the mixture. This may ensure the interaction between the reactivated cholinesterase inhibitor and the cholinesterase has no inhibition or interference from the agent such as fluoride ions which may affect accurate detection of the cholinesterase inhibitor.

The method may further comprise a pre-measurement step wherein the cholinesterase activity is measured before step (a). This may involve measuring this cholinesterase activity before it is in contact with any sample resulting in a known cholinesterase activity that may be referred to as the maximal cholinesterase activity. The known cholinesterase activity then provides a cholinesterase activity independent of an individual's pre-exposure level of cholinesterase. As the detection method measures any activated cholinesterase inhibitor present rather than the level of blood cholinesterase the variation in such blood levels between individuals does not factor into the detection. The cholinesterase may further be washed with a wash buffer such as a phosphate buffer before measurement of the cholinesterase activity before step (a). The contents of the wash buffer may require the presence of non-ionic surfactants to stabilise the immobilised cholinesterase activity. The pre-measurement step to determine the maximal cholinesterase activity may comprise a chromogenic assay mixture comprising: a substrate such as a choline, for example acetylthiocholine (ASCh), butyrylthiocholine, or acetylthiocholine iodide (ASChI); and a chromogen such as 5,5'-dithio-bis-2-nitrobenzoc acid (DTNB), or 4,4-dithiodipyridine or pyridine disulphide (PDS) or 2,6-Dichloroindophenol (DPIP). The assay may be performed at ambient temperature to 37° C. and optimally at pH 7.3 to 8.0. The cholinesterase activity may be measured spectrophotometrically in the range of 320 to 610 nm and preferably at 412 nm where DTNB is the chromogen or 324 where PDS is the chromogen or 606 nm where DPIP is the chromogen using the Ellman's method, for example with a microplate reader. The change in absorbance may be determined with kinetic reading with the rate in the change in absorbance being correlated to the activity of the enzyme, calculated using the Ellman equation and constants.

The method may further comprise a protein precipitation step before step (a.1) wherein high concentrations of salt are used to salt out or precipitate out the proteins. The salt may include, citrate, phosphate, sulphate, acetate, chloride, nitrate, thiocyanate or ammonium sulphate. The high concentration may be a saturated salt such as saturated ammonium sulphate (SAS). The salt may remove endogenous proteins including blood proteins where said sample includes blood. This is to prevent the reactivated cholinesterase inhibitor from further interactions with any free cholinesterase in the blood sample. A saturated Salt could be in the range of 1 to 10 volumes with respect to the sample volume or more preferably in the range of 2.5 to 7 volumes or 2.5 to 6 volumes or most preferably in the ratio 5:1 volume of saturated salt to sample. The method can include any alternate methods of protein removal such as ultra-filtration etc.

A cholinesterase inhibitor suppresses the action of a cholinesterase enzyme such as acetylcholinesterase (AChE), or Pseudocholinesterase (BChE or BuChE), also known as plasma cholinesterase. Cholinesterase inhibitors include nerve gases such as sarin (GB), Soman (GD), Tabun (GA), Cyclosarin (GF), VR and VX, some snake venoms, TEPP, DFP, organophosphate pesticide such as dichlorvos, organosulfur and carbamate pesticides. A cholinesterase inhibitor is reactive and in a sample containing naturally occurring cholinesterase it is less likely to be in an active state and likely to be bound to the cholinesterase enzyme. It must be reactivated or regenerated by disrupting the interaction between the cholinesterase inhibitor and cholinesterase in the sample.

The reactivation of a cholinesterase inhibitor further comprises an incubation step before step (a.1) wherein the sample is incubated together with the agent capable of recovering a cholinesterase inhibitor and or an acetate buffer for anywhere between a few second to 1 hour or more preferable 3 to 40 minutes, or most preferably for 20 to 40 minutes before it is filtered and or addition of a saturated salt solution. A sealing tape such as an aluminium sealing tape may be placed over the sample during the incubation step.

The method may be used on a plurality of samples at the same time. This may be 2 or more samples or many more such as 96 in a 96-well filtration plate comprising an inert hydrophilic filter.

The method may further comprises an inhibition step (b.1) before step (c) wherein the activated cholinesterase inhibitor is left to inhibit the cholinesterase for about 1 to 20 minutes or more preferably 5 to 15 minutes, or most preferably for 5 minutes to reduce the detection time or 15 minutes to achieve better inhibition. The inhibition step may optionally be conducted on a plurality of samples that may be 2 or many more such as 96 in a 96-well plate.

The method may further comprise a washing step (b.2) before step (c) wherein the immobilised cholinesterase is washed with a buffer such as saline or phosphate buffer containing a non-ionic surfactant such as Triton, Polyoxyethylene sorbitan monolaurate Solution or Tween, more specifically Tween-20 or Triton X-100. The washing step may be just once or it may be repeated 1 to 10 times or more with a minimal effect on detection of the cholinesterase inhibition.

Measurement of the cholinesterase activity to determine the inhibition of cholinesterase activity from the known activity may be done with a chromogenic assay mixture comprising: a substrate such as a choline salt, for example acetylthiocholine (ASCh), butyrylthiocholine, or acetylthiocholine iodide (ASChI); and a chromogen such as 5,5'-dithio-bis-2-nitrobenzoc acid (DTNB), or 4,4-dithiodipyridine or pyridine disulphide (PDS) or 2,6-Dichloroindophenol (DPIP). The assay may be performed at ambient temperature to 37° C. and optimally at pH 7.3 to 8.0. The cholinesterase activity may be measured spectrophotometrically in the range of 320 to 610 nm and preferably at 412 nm where DTNB is the chromogen or 324 nm where PDS is the chromogen or 606 nm where DPIP is the chromogen using the Ellman's method, for example with a microplate reader. The change in absorbance may be determined with kinetic reading with the rate in the change in absorbance being correlated to the activity of the enzyme, calculated using the Ellman equation and constants. This activity is then compared to the known cholinesterase activity to determine if there is a change in the activity. A change in the cholinesterase activity from the known activity may indicate exposure of an individual to a cholinesterase inhibitor.

A second aspect of the invention provides a kit for detection of a cholinesterase inhibitor in a sample comprising; an agent capable of recovering a cholinesterase inhibitor-cholinesterase mixture.

The agent capable of recovering a cholinesterase inhibitor from a sample comprises a reactivity towards phosphyl moieties such an agent may include an active site of an oxime or fluoride ions, Magnesium ions, Cobalt ions, Nickel ions, Metal salts such as Ammonium Molybdate, copper sulphates including copper kelates, and the like. Concentrations of fluoride or other ions may be used in the range 1 mM to 2M. Recovering a cholinesterase is best done at an acidic pH. Potassium fluoride (KF) may be used preferably acidified by an acetate buffer. The volume of acetate buffer with respect to the sample volume is in the range of 2 to 6 or more preferably in the range 3 to 5, or 4 to 4.5 or most preferably a volume of 4.5.

A cholinesterase is an enzyme. There are two naturally occurring cholinesterase: Acetylcholinesterase (AChE), and Pseudocholinesterase (BChE or BuChE). There are several cholinesterase enzymes commercially available typically from animal or marine sources such as horse, cow, electric eels, other erythrocytes and the like. The cholinesterase used may be from any of these sources including non-human and human sources. The cholinesterase may also be the peptide component of the active site capable of interaction with a cholinesterase inhibitor. The cholinesterase may further be dehydrated as this may increase its shelf life.

The cholinesterase may further be immobilized on a support as this may increase its shelf life and portability. The support may be glass or polymer comprising a plurality of detection sites that may be 2 or more detection sites and may include walled columns or tubes, or welled plates such as 96-well plates. The support may comprise an element that facilitates immobilization of a protein, such as biotin, amino surface, an activated surface for covalent binding or other such methods known in the art. For example a biotin-coated support such as biotin-coated 96-well plates may have a cholinesterase immobilised on the support via a cholinesterase-avidin/streptavidine conjugate binding to biotin.

The kit may further comprise a saturated salt solution.

The kit may further comprise chromogenic reagents comprising a substrate reagent and a chromogen reagent. The chromogenic reagents may further be dehydrated. A buffered solution may further be provided to reconstitute the dehydrated chromogenic reagents for use in the field.

The kit may further comprise a buffered solution such as saline or phosphate buffer containing a non-ionic surfactant such as Triton, Polyoxyethylene sorbitan monolaurate Solution or Tween, more specifically Tween-20 or Triton X 100. The kit may further comprise a spectrophotometer such as a microplate reader.

The kit may further comprise a vacuum pump, and a vacuum filtration manifold.

The kit may further comprise an 8 channel pipette, pipette tips, safety lancets, capillary tubes such as heparinised capillary tubes, an alcohol swab, a plaster aluminium sealing tape and or disposable gloves.

The kit may further comprise a microplate reader and or a laptop.

A third aspect of the invention provides a method of manufacturing a kit for detection of a cholinesterase inhibitor in a sample comprising; preparing an agent capable of recovering a cholinesterase inhibitor from a sample and preparing and stabilising a cholinesterase on a support or platform.

Preparing an agent capable of recovering a cholinesterase inhibitor from a sample comprises making a 1 mM to 2M solution of the agent having a reactivity towards phosphyl moieties such as an active site of an oxime or fluoride ions, or molybdite ions, Magnesium ions, Cobalt ions, Nickel ions, Copper salts such as copper sulphates including copper chelates, and the like in an acidic buffer. The agent may be a Potassium or sodium fluoride (KF or NaF) in an acetate buffer.

Preparing a cholinesterase comprises packing or maintaining the cholinesterase in a way that it may be stable. This may include fresh isolation before immediate use, refrigeration or freezer storage, dehydration, immobilisation and or vacuum packaging. The cholinesterase may further be immobilized on a support as this may increase its self life and portability. The support may be glass or polymer comprising a plurality of detection sites that may be 2 or more detection sites and may include walled columns or tubes, or welled plates such as 96-well plates. The support may comprise an element that facilitates immobilization of a protein such as biotin, amino surface, EDC/NHS, an activated surface for covalent binding or other such methods known in the art. For example a biotin-coated support such as biotin-coated 96-well plates may have a cholinesterase immobilised on the support via a cholinesterase-avidin/streptavidin conjugate binding to biotin.

To immobilise cholinesterase on a support or platform the cholinesterase such as an Acetylcholinesterase (AChE) is coupled to avidin or streptavidin molecule using a conjugate that cross-links to free amino groups of the proteins such as glutaraldehyde (GA). The avidinated AChE may be added to the surface or platform coated with biotin. This may further be left to incubate for 12 to 48 hours or more preferably 18 to 32 hours or most preferably 24 hours at cold temperatures in the range of 10 to 1° C. or preferably 4° C.

Following incubation, the surface or platform containing the immobilised cholinesterase may be washed with a Wash Buffer comprising a buffered solution such as saline or phosphate buffer containing a non-ionic surfactant such as Triton, Polyoxyethylene sorbitan monolaurate Solution or Tween, more specifically Tween-20 or Triton X 100 and or BSA. This may remove unbound cholinesterase. The activity of the immobilised cholinesterase may be determined for quality control and may then be washed further to remove traces of the activity assay mixture.

The method of manufacture may further comprise adding a protective coating to protect the immobilised cholinesterase. The protective coating may comprise trehalose, gelatin and or sodium azide. This may be in the concentration 10% (w/v) trehalose, 0.1% (w/v) gelatin and 0.02% (w/v) sodium azide. The protective coating may be placed onto the immobilised enzyme for 2 to 6 hours or preferably 4 hours at cold temperatures in the range of 10 to 1° C. or preferably 4° C. Excess protective coating may be removed by decanting, The cholinesterase may be dehydrated for example lyophilised at a temperature of −40° C. for 12 to 48 hours or more preferably 18 to 32 hours or most preferably 24 hours for long term stable storage.

The cholinesterase may be stored under vacuum as it may help to prevent the fast degradation of the enzyme activity. The vacuum may be vacuum-packing in a bag. Vacuum bags may include transparent vacuum bags used for storage of food, normally made of polypropylene material or those used in the electronics industry for packing of moisture-sensitive electronic parts such as a moisture-barrier bag called MB bags. The vacuum bag may further comprise aluminium backing as this may protect the components stored inside from both moisture and light. This may have the advantage of extending the shelf life of the cholinesterase used in the detection and may be much cheaper to manufacture than other methods of detection of regeneration of a cholinesterase inhibitor such as with a GC-MS.

The method of manufacture further comprises preparing a chromogen reagent and a substrate reagent for chromogenic detection of a cholinesterase inhibitor. The substrate reagent may be a choline, for example acetylthiocholine (ASCh), butyrylthiocholine, or acetylthiocholine iodide (ASChI); and the chromogen reagent such as 5,5'-dithio-bis-2-nitrobenzoc acid (DTNB), or 4,4-dithiodipyridine or pyridine disulphide (PDS). Normally heat-sensitive reagents like the enzyme AChE or the substrate reagent ASChI require extreme cold storage less than −20° C. For ASChI, which is hygroscopic, light-sensitive and easily subjected to self-hydrolysis by thiocholine, it may be stabilised by dehydration such as lyophilisation. Both the substrate ASChI and chromogen DTNB may be lyophilised together this may be for 12 hours to 3 days depending on the strength of the lyophiliser. The dehydrated chromogenic reagents may be tested for quality control of the dehydration procedure by storage at 45° C. for up till 8 weeks or 6 months followed by examination of the reagents to detect any change. The dehydrated reagents may be reconstituted with a buffered solution such as saline or phosphate buffer preferably at pH 7.2 to 8.0 and may be compared to the normal freezer stocks of the chomogenic reagents.

The method of manufacture may further comprise packing the components of the kit into one or more transit case.

The invention is able to detect the presence of a cholinesterase nerve enzyme inhibitor within blood and other samples, in both free and blood proteins-bound form. Since cholinesterase nerve enzyme inhibitors do not normally exists in healthy, non-exposed human subjects, this invention permits validation of trace exposure to cholinesterase nerve enzyme inhibitors without the need for prior baseline establishment. This invention employs a novel protocol that stabilizes and recovers the cholinesterase nerve enzyme inhibitor, in both free form or reactivated from blood samples, into a formulation suitable for selective inhibition of immobilised cholinesterase enzyme and without cross-interference from blood cholinesterases or free fluoride ions. A loss of immobilised cholinesterase enzyme activity, as visualized by absence of coloured-hydrolysis product from added substrate solution, would be correlated to the concentration of the recovered cholinesterase nerve enzyme inhibitor to which the immobilised cholinesterase was exposed.

The invention enables clear, on-site rapid detection of multiple samples for trace levels of cholinesterase inhibitors in either the free form or reactivated from blood protein-bound form. In the free form within the blood samples, detection limit is down to 0.962 nM of nerve enzyme inhibitors, which may include nerve agents (e.g., sarin and VX) and organophosphorus pesticides (e.g., dichlorvos). In the blood protein-bounded form, detection limit is 1.472 nM of regenerated inhibitor for samples of cholinesterase complexed with nerve enzyme inhibitors such as nerve agents (e.g., sarin and VX) or organophosphorus pesticides (e.g., dichlorvos). At such trace levels, observed blood cholinesterase inhibition was 22.9% of baseline and there was no free cholinesterase inhibitor present in the sample. The invention permits selective detection for nerve agents and organophosphorus pesticides present in blood samples and is not affected by carbamates for example pyridostigmine up to $7\times10^{-4}$ mM with weak inhibitory effects on cholinesterase. The invention also permits detection of OP cholinesterase inhibitors present in blood samples in the presence of treatment drugs such as oxime reactivators (e.g., 2-pralidoxime chloride) at whole blood concentrations up to 0.266 mM. This in vitro plasma concentration of oxime is attainable from 7×autoinjector doses (600 ug per autoinjector) of 2-pralidoxime chloride.

Unlike in laboratory conditions where multiple test tubes and chromatographic methods may be available to isolate compounds of interest this invention instead allows a person in field conditions to remove all the unwanted and interfering elements in just one test location. This is almost a reverse isolation that allows on the spot recovery of cholinesterase inhibitor from a sample.

The technology can be used readily by a person having ordinary or minimal skill in the area of technology related to the invention. The equipment required to execute this technique is light weight, portable and less expensive than laboratory based equipment such as a GC-MS. This may additionally include equipment such as a small diaphragm suction pump, a portable microplate reader and a portable aspiration and washing sample processor. These equipment are either readily available in all hospitals and can also be packed neatly into military vehicles such land-rovers or emergency service vehicles.

To overcome current limitation in front-end triage, this high-throughput diagnostic system was developed for mass screening of potential casualties. The diagnostic kit of the invention requires only small samples for example 20 μl of capillary blood for diagnosis and has a screening throughput of multiple casualties within 30-40 minutes which excludes sample collection and patient data entry.

Non-Limiting Illustration of the Invention

A high throughput diagnostic kit for the validation of nerve agent exposure such as sarin and organophosphate pesticide such as dichlorvos exposure has been developed. The Current test diagnostic kit can diagnose up to 96 persons within 30-40 mins which excludes sample collection and patient data entry. The microplate reader and accessories is packed into 2 watertight protector transit cases, each weighing less than 13 kg. The microplate assembly within the transit case has undergone Environmental Qualification Test (EQT) including vibrations and shock to simulate transport of equipment to field. The microplate assembly has successfully passed all tests parameters in the EQT.

Materials and Methods

Materials

Acetylcholinesterase from electric eels, *Electrophorus electricus* (AChE, EC 3.1.1.7) and sodium azide were from Fluka, Switzerland. 5,5'~dithio-bis-2-nitrobenzoic acid (DTNB), acetylthiocholine iodide (ASChI), glutaraldehyde (GA), albumin bovine fraction V (BSA: bovine serum albumin), gelatin type B, D(+)-trehalose, and potassium fluoride were obtained from Sigma, USA. Avidin was purchased from ICN Biomedicais Inc, USA. Ammonium sulphate, disodium hydrogen phosphate, sodium dihydrogen phosphate, potassium, Triton X-100, and alumina (aluminium oxide) were from Merck, Germany. The biotin-coated 96-well plates (Recti-Bind™ Biotin Coated Microwell Strip Plates) were purchased from Pierce, USA. The microplate was used for monitoring of presence of nerve agent(s) which inhibit the immobilised AChE.

Human blood was obtained through venous phlebotomy laboratory volunteers and stored in heparinised vacutainer tubes. Capillary blood obtained via finger-prick was used immediately without storage. Sarin (GB) was synthesised in-house by the Synthesis Team in DSO National Laboratories.

All buffers were prepared with Milli-Q deionised water and autoclaved or filtered through 0.2 um prior to use. In the immobilising step, all reagents were prepared using 0.1 M phosphate buffer pH 7.2. In the determination of enzyme activities, 0.1 M phosphate buffer (pH 8.0) was used. Stock solutions of 1 mg/ml AChE were prepared in 0.1 M phosphate buffer pH 7.2 and kept in aliquots at −80° C. ASChI (100 mM) and DTNB (10 mM) stocks were prepared in 0.1M phosphate buffer pH8.0 and kept in aliquots at −80° C. Reagents were diluted as required in 0.1 M phosphate buffer and kept on ice for the duration of experiment. Ammonium sulphate was dissolved in milli-Q water with heating till saturated and used as 100% (w/v) solution ie: saturated ammonium sulphate buffer (SAS buffer).

Protocol for Immobilising Cholinesterase Enzyme (ImmAChE)

One method of immobilising AChE involved coupling AChE to avidin using glutaraldehyde (GA) that cross-linked to free amino groups of the proteins. The avidinated AChE was added to the biotin plates and left to incubate for 24 hours at 4° C. Following incubation, the platforms were washed extensively with Immobilisation Wash Buffer (phosphate buffer with Tween 20 and BSA) to remove unbound AChE. The activity of the immobilised AChE was determined. The plates were washed 3 times further to remove any traces of the assay mixture. To protect the immobilised AChE, a protective coating consisting of 10% (w/v) trehalose, 0.1% (w/v) gelatin and 0.02% (w/v) sodium azide was placed onto the immobilised enzyme for 4 hours at 4° C. After incubation, excess protective coating was removed by decanting, and the immobilised enzyme was lyophilised at −40° C. for 24 hours for long term stable storage of diagnostic kit.

Protocol for Determination of Cholinesterase Enzyme Activity

To determine the activity of AChE, the assay mixture contained 0.45 mM ASChI as substrate and 0.3 mM DTNB as chromogen in 0.1 M phosphate buffer pH8.0. All assays of AChE activities were performed at 37° C. and pH 8.0. All concentrations reported were final concentrations.

For AChE immobilised on biotin plate (thereafter termed as ImmAChE), AChE activities were measured spectrophotometrically at 412 nm using the Ellman's method, with a microplate reader (e.g., Molecular Devices Spectra Max™ 250). The change in absorbance was determined with kinetic reading over the course of 2 minutes with 12-second intervals. The activity of the enzyme is calculated using the following equation and constants:

$$\text{Activity}(\mu\text{mole-min}^{-1}\cdot\text{ml}^{-1})=\Delta\text{Absorbance}(\text{Au/min})\times 1/(\epsilon b)\times 1/1000$$

where

ΔAbsorbance=Rate of Change in absorbance b=path length in cm, and $\epsilon$=13.6 $\mu$mole$^{-1}$ ml cm$^{-1}$ Determining Presence of Nerve Enzyme Inhibitor Using the Immobilised Cholinesterase Kit Activities of immobilised cholinesterase within microtiter wells were determined prior to the addition of samples. Samples were then added onto microtiter wells containing immobilised cholinesterase and inhibition reaction was permitted to proceed for defined intervals (5 min, 10 min, 15 min and 30 min). Samples were aspirated off using vacuum suction and immobilised cholinesterase plates rinsed with the Wash Buffer. Residual enzyme activity within microtiter well is then determined and the difference in cholinesterase activity correlated directly to amounts of nerve enzyme inhibitor in the sample.

With the OP-AChE Complex regeneration step, the diagnostic kit is capable of detecting even protein-bound OP chemicals from blood, with a screening throughput of 96 blood samples within 30-40 minutes of sample receipt. Percentage reduction of enzyme activity is correlated indirectly to the amount of nerve enzyme inhibitor present.

Optimising of Current Test Technology

There were many parameters of the protocol to be optimised. The protocol optimisation was performed on a microplate reader. The parameters optimised include:
1. Initial Feasibility Testing And Evaluation Of 96-Well Filtration Plates For Regeneration Procedure And Selection Of Best Membrane
2. Reducing Blood Volume
3. Concentration of KF in Regeneration Buffer
4. Volume Of Regeneration Buffer
5. Regeneration Step Incubation Time
6. Amount Of Alumina
7. Minimal Inhibition Time Required
8. Effects Of Washing
9. Components Of Wash Buffer
10. SAS Precipitation Step Incubation Time
11. Volume of SAS to Blood Ratio
12. Influence of Shuffling Fluoride Removal and Blood Protein Precipitation Steps In Vitro Human Blood Experiments: Measurement of Blood Acetylcholinesterase Inhibition and Current Test Response with Addition of Sarin, VX, Tabun or Dichlorvos Detection for Sarin, VX, Tabun and the organophosphate pesticide Dichlorvos spiked into human blood samples was carried out with the optimised current test technology. Various amounts of Sarin, VX, Tabun or Dichlorvos samples were spiked into whole blood and allowed to incubate for durations of 5 min, 15 min, 30 min or 24 h. Amounts of Sarin, VX, Tabun or Dichlorvos was titrated such that there is no free nerve agent or pesticide available at the end of the incubation process, as determined by inhibition of the immobilised enzyme plate. For each analysis, at least 3 repeat analyses were carried out and the mean results determined together with the standard error of the mean.

A. Determination of Threshold Value for Non-Specific Inhibition of Immobilised AChE by Normal Blood Samples In order to determine the true detection window of this diagnostic kit, it is important to first determine the threshold value for acceptable non-specific inhibition of ImmAChE wells by normal blood samples that do not contain nerve agents or nerve enzyme inhibitors.

B. Determining Limit of Detection (LOD) of Current Test Diagnostic Kit

With the final optimised Current test kit protocol and specified threshold for positive detection, the detection sensitivity of the Current test diagnostic kit was tested with various concentrations of Sarin, VX, Tabun or Dichlorvos spiked in human blood.

Validation Current Test Kit Test Protocol to an Asymptomatic Challenge of Sarin in a Laboratory Rat Model An in vivo study was carried out with young male Sprague Dawley laboratory rats administered with an asymptomatic dose of sarin (0.4×LD50; subcutaneous; 50 ug/kg). Three animals were evaluated and dose selected was based on previous studies that indicated at this dose, there will be no clinical symptoms of intoxication (Shih T M et al. Cerebral acetylcholine and choline contents and turnover following low-dose acetylcholinesterase inhibitors treatment in rats. *Archives of Toxicology* 2006; 80(11):761-767). Blood samples were withdrawn at periodic intervals from the animal from an indwelling catheter inserted into the carotid artery and tested with current test kit for presence of sarin nerve agents. Sarin treated animals were observed for 24 h before being euthanized at the end of the observation period.

Determining Current Test Response to Sarin in Human Blood Samples in the Presence of Pyridostigmine and Oxime Reactivator, 2-Pralidoxime Chloride The ability of the Current test kit to detect cholinesterase in the presence of various amount of a prophylactic drug such as pyridostigmine or a treatment drug such as an oxime reactivator was added with sarin to human blood and samples were tested. The amount of pyridostigmine in the blood was up to 7 fold the prescribed dose. The oxime added was double the prescribed number of autoinjector doses of 2-PAM.

Validating Identity and Quantity of Nerve Agent Regenerated from Human Blood Sample Using Current Test Kit Protocol with Solid Phase Extraction and Gas Chromatography Techniques Samples treated by the Current test Protocol as indicated above is removed at Step vii and extracted by reversed phase C18 cartridges. A volume of 20 ml of test sample was passed into each solid phase extraction cartridges and eluted with 1 ml of ethyl acetate. Internal standard was added to eluted sample to correct for variances in volume of sample recovery. Eluted solution was analysed by gas chromatography attached with a mass spectrometer detector. Gas chromatographic analyses were performed either with a Hewlett Packard GCMS system. Separation was carried out using a DB-5MS column, 30 m×0.25 mm i.d., 0.25 μm film thickness. Splitless injection with 5 μl injection volume was performed at 200° C. The temperature program was initial temperature of 40° C., hold for 2 min, programmed at 10° C./min to 150° C. and heated again at new rate of 20° C./min to 290° C. and held for another 2 min. Total run time was 22 min. The carrier gas was helium at 36 cm/s. Sarin standards analyses were performed initially using GCMS (EI)—full scan mode. For sensitive quantification analysis of regenerated sarin obtained from blood samples, selection ion monitoring was adopted with GCMS (EI) mode, with the following ions of m/z 125, 99, 81 monitored for sarin.

Identity of eluted peaks was identified by mass spectrum as well as retention time relative to an introduced internal standard. The percentage recovery efficiency of the solid phase extraction process was determined and used to determine the amount of Sarin regenerated, using the Current test kit Protocol, from a human blood sample having a final spiked concentration of 100 nM Sarin. This data is compared to the results determined from Current test kit Protocol and hence used to reaffirm its accuracy.

Ruggedisation of Laboratory-Based Microplate Reader for Field Use

To meet the requirement for deploying this Current test diagnostic kit in the field, the entire test kit is packed into two transit cases and environmental qualification tests were performed on the microplate reader packed in the transit case. The environmental qualification tests performed are based on MIL-STD-810E (Environmental Test Methods and Engineering Guidelines), for shock and vibration. The guidelines for the secure assembly of microplate reader in the transit case were based on MIL-STD-108E (Definitions of and Basic Requirements for Enclosures for Electric and Electronic Equipment).

Current Test Kit Reagents Preparation and Packaging Issues

An important consideration for the eventual deployment of this diagnostic kit is the stability of the reagents. The reagents used for enzymatic assay are biologics and hence are easily degraded under normal room temperature conditions. A humid environment can cause rapid degradation of reagents like AChE, even when it has been immobilised and stabilised through lyophilisation procedure. Preliminary results indicated that ImmAChE stored under vacuum helped to prevent the fast degradation of the enzyme activity. Hence, all lyophilised reagents (ImmAChE plate and substrate/chromogen) were vacuum-packed to enhance reagents stability.

Two types of vacuum bags were evaluated for enhancing the stability of ImmAChE. One type is the normal transparent vacuum bags used for storage of food, normally made of polypropylene material, and hence called PP bags. Another type is those used in the electronics industry for packing of moisture-sensitive electronic parts. It is a moisture-barrier bag (called MB bags), with aluminium backing, so that it protects the components stored inside from both moisture and light. Results of this evaluation will be reported.

Development of Software for Rapid and Easy Management and Interpretation of Assay Data by Paramedics After assaying each plate on a microplate reader, the raw data (kinetic velocity) generated by the Biorad's Microplate Manager Software has to be processed before data could be interpreted. To permit rapid and ease of data interpretation, an Excel template containing the necessary algorithms to calculate whether a person has been exposed to nerve agent sarin, was developed to manage the reader raw data.

Results and Discussion

Optimising Current Test Technology

To increase the number of samples processed within a short timeframe, a 96-well Immobilised AChE plate concept was compared against the original single glass vial immobilised cholinesterase platform. For removal of endogenous blood proteins, the method of SAS precipitation of proteins (used in the portable system) was developed in place of the laboratory ultra-filtration method, which thus eliminated the need for deployment of bulky equipment such as centrifuge for the ultra-filtration process.

As alumina removes free fluoride ions it will affect the eventual success of ImmAChE inhibition by reactivated sarin, much effort was placed on sourcing for a 96-well format platform to simultaneously process 96 samples. With the original laboratory-based method, in-house prepared alumina columns were crudely made and the alumina column preparation process highly laborious. Each 1.0 ml syringe barrel was fitted with a frit made of flimsy filter paper before being filled with pre-weighed alumina. A small tube was then fitted at the bottom of the syringe to collect filtrate after centrifugation. Furthermore, this process does not truly allow simultaneous processing of 96 samples, as the centrifuge only allows 10 syringes to be centrifuged at any one time.

A filtration device was identified that can process up to 96 samples simultaneously. This requires the use of a small vacuum pump and a specialised filtration manifold for filtering 96-well filtration plates (FIG. 1). Further details of the elaborate method optimization is described below:

1. Initial Feasibility Testing and Evaluation of 96-Well Filtration Plates for Sarin Regeneration Procedure and Selection of Best Membrane As blood is a complex matrix with lots of endogenous proteins, and with addition of SAS to precipitate the proteins, it is easy to clog normal filtration plates. Initial feasibility testing of using a 96-well filtration plate combined with a filtration vacuum manifold for the nerve agent regeneration protocol was done with Millipore MDRL NP4 plates. The hydrophobic nature of PTFE membrane for this plate was pre-treated to be hydrophilic and it comes with a pre-filter to block off large debris, so that the 0.45 μm PTFE membrane will not be so easily clotted. We were able to obtain successful sarin regeneration that resulted in the inhibition of ImmAChE plate with a not-yet-optimised regeneration protocol (Data not shown). However, just as we were to proceed with protocol optimisation to enhance the detection limits using this method, we received news from the supplier Millipore that they have discontinued this product line. Hence we had to evaluate other types of plates.

Table 1 summarised the types and brands of filtration plates being evaluated. We discovered that even though diluted and precipitated blood will clog most membranes types, the addition of alumina powder to the filtration plate help to act as a pre-filter, so that the membranes were not clogged. PVDF membrane was the membrane of choice due to its hydrophilic nature, good physical strength and good chemical resistant. Ideally an inert hydrophilic filter was preferred where inert or chemically resistant in some cases may include a small amount of Teflon or gold or other inert substances but not so much that it would reduce the movement of water through the filter. A hydrophilic filter will allow aqueous solutions to pass through. Some examples of an inert hydrophilic filter comprise Nitrocellulose membrane such as those with a 0.45 μm or larger pore size, PolyVinyliDene Fluoride (PVDF) or Polytetrafluoroethylene (PTFE) such as those with a 0.45 μm or larger pore size that are at concentrations that are hydrophilic in nature.

Figure 2:
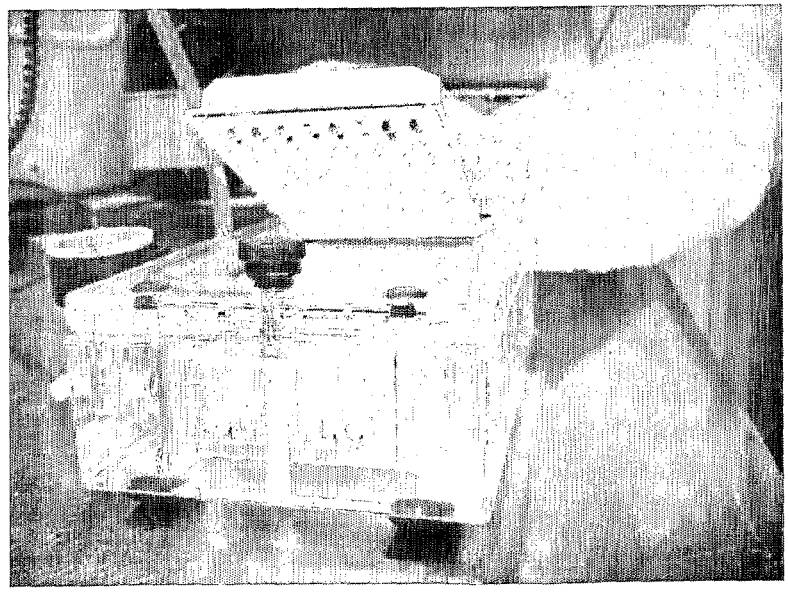
FIG. 2: An Example of an inert hydrophilic membrane filter that allows no "bubbling and splattering" of filtrate to minimise" cross contamination of wells. Droplets of liquid are observed at the well bottoms after filtration for Whatman 7700-3306 filtration plate, which required careful removal of filtration plate to avoid cross-contamination.
Figure 3:
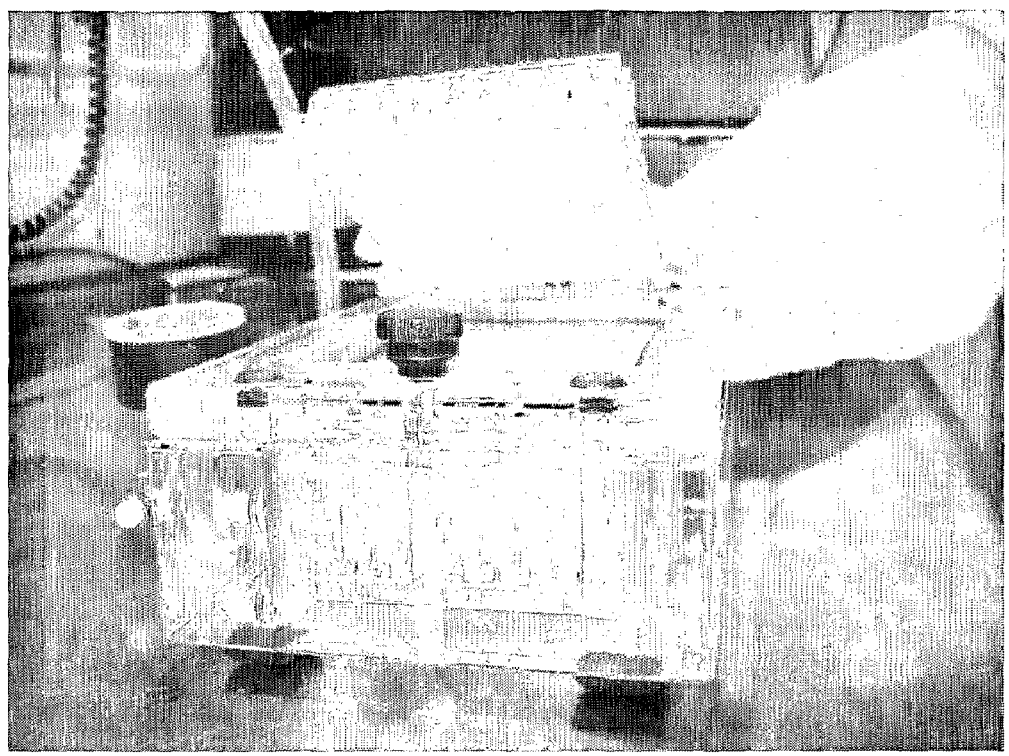
FIG. 3: An example of an inert hydrophilic membrane filter that allows no cross contamination of wells. A much cleaner well bottom was observed for Millipore MSHV N45 filtration plate after filtration procedure as no droplets were seen at the well bottoms.

For PVDF membranes, even though Whatman 7700-3306 filtration plate resulted in a droplet of filtrate at the tip of each well bottom after filtration (see FIG. 2), it was initially chosen over Whatman 7700-2806 due to no "bubbling" of filtrate and cross-contamination of wells (suspected to be due to the long drip of Whatman 7700-2806). The Whatman 7700-3306 was hence used for majority of protocol optimisation experiments, whereby the filtration plate had to be very carefully lifted from the vacuum manifold after filtration to a paper towel immediately to prevent the each droplet from dripping into other wells causing cross-contaminations. It was only much later that the more effective Millipore MSHV N45 filtration plate (also PVDF 0.45 μm membrane) was delivered and more tests could be conducted. There was no liquid droplet at each well bottom after filtration due to the unique design of the Millipore filtration plate, and thus this prevented the messy process of blotting each plate with paper towels, and more importantly, greatly prevent cross-contamination between wells (FIG. 3).

2. Reducing Blood Volume

The blood volume required in the initial Current test kit test kit was 200 μl, before we further decreased it in the laboratory to 50 μl with 96-well assay plate format. We attempted to reduce the volume of blood required for the new Current test test kit as it is sometimes difficult to obtain a few drops of blood from a relatively painless finger-prick (either we had to choose a lancet that has deeper penetration which in turn will increase pain, or the finger has to be squeezed harder and for much longer).

Figure 4:
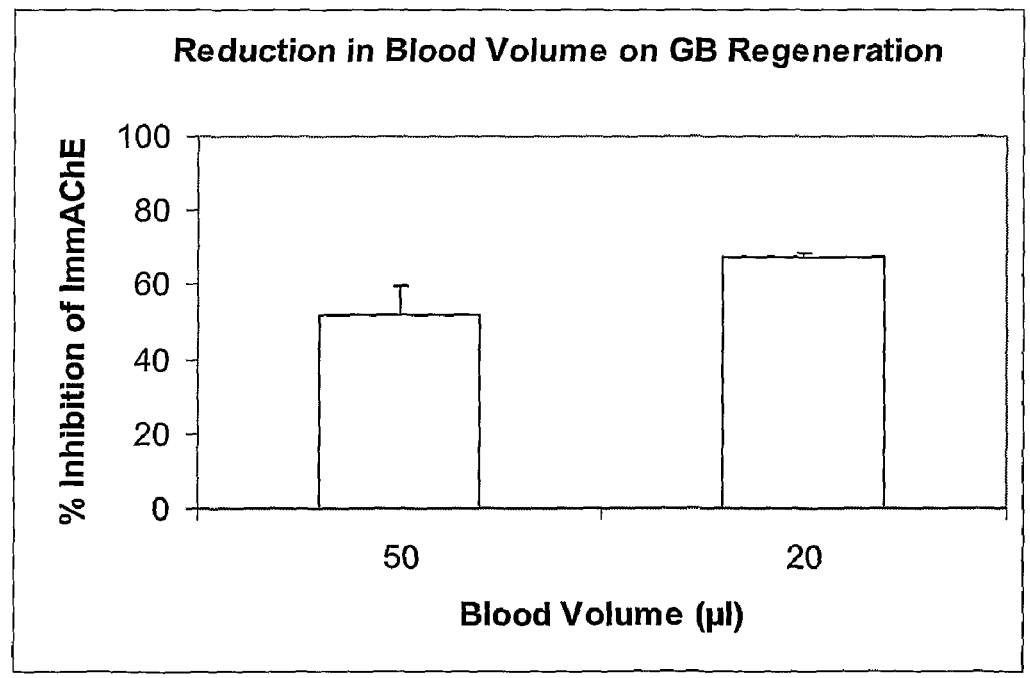
FIG. 4: Detection of Cholinesterase inhibitor using different blood sample volumes.

Blood volumes of 20 μl and 10 μl were tested out in comparison to the original laboratory-based method of 50 μl, as these volumes can be accurately collected with commercially-available 20 μl or 10 μl end-to-end heparinised capillaries. All the volume ratios were kept the same with the exception of alumina amount, which had to be reduced much more due to dead volume being trapped by the alumina after filtration. Table 2 showed the exact volumes of all reagents used and the approximate volume of filtrate available after filtration. With a starting volume of 10 μl blood, it was difficult to achieve enough and reproducible amount of filtrate and hence we opted for the 20 μl blood instead. FIG. 4 showed that the sarin regeneration can be achieved with a lesser blood volume of 20 μl sarin-spiked blood instead of 50 μl.

FIG. 4 shows a comparison of sarin regeneration with either 50 μl or 20 μl blood. Sarin-spiked blood was incubated with 1.5 volumes of acetate buffer with KF, followed by addition of SAS. Resultant mixtures were filtered through either 0.45 g or 0.1 g alumina for 50 µl blood and 20 µl blood respectively. ImmAChE were inhibited with filtrate for 20 mins, followed by washing, and final assay for remaining ImmAChE to indicate the amount of ImmAChE that was inhibited. Even though the filtrate volume from 20 µl blood was lesser, there was no reduction in the inhibition as compared to 50 µl blood.

3. Concentration of KF in Regeneration Buffer

To increase the yield of regenerated nerve agents from inhibited blood samples, both VX-inhibited and Sarin-Inhibited human blood samples were incubated with a range of [KF] for 5 minutes before the samples were further processed in accordance with Current test kit Protocol. Four repeats were carried out for the VX investigations while the follow-up investigations with Sarin were carried out with 2 repeats. The data (FIG. 5) revealed that regeneration and detection by Current test kit of the fluorinated version of VX and Sarin from inhibited human blood samples was most successful with 50 nM of KF in the regeneration buffer.

4. Volume of Regeneration Buffer

The ratio of acetate buffer to blood volume directly affects the acidity of blood matrix during nerve agent regeneration by fluoride ions and hence plays an important part in the success of the test kit. In Project Scent, the ratio of acetate buffer to blood used was 1.5:1 to 2:1. Preliminary experimental trial with acetate buffer 1.5 times and 3 times more than blood volume indicated that more sarin was activated with 3:1 acetate buffer:blood (data not shown). Hence we increased the acetate buffer to blood ratio to find out the optimal volume of acetate buffer required for sarin regeneration.

FIG. 6 demonstrates the range of varied ratios of acetate buffer volume to blood volume on sarin regeneration. Blood was spiked with 100 nM sarin. After 30 mins, 20 µl of blood was added to 3, 4, 4.5 and 5 blood volumes of acetate buffer containing KF (60 µl, 80 µl, 90 µl and 100 µl respectively) and incubated 5-15 mins. SAS was to precipitate blood proteins and the resultant mixture was filtered through a 96-well Whatman PVDF filtration plate containing 0.1 g alumina, directly onto ImmAChE plate and incubated for 5 mins. The plate was then washed to remove filtrate and assayed for

TABLE 1

Table comparing the types of filtration plates evaluated for sarin regeneration protocol.

| Brand/Catalogue# | Description | Membrane Type/Pore Size | Remarks |
|---|---|---|---|
| Millipore MDRL NP4 | Multiscreen Deep Well Solvinert (2 ml) with Pre-filter | PTFE hydrophilic 0.45 µm | Successful sarin regeneration but Millipore discontinued production. |
| Millipore MSRP N04 | MultiScreen Solvinert (500 µl), no Pre-filter | PTFE hydrophobic 0.45 µm | No filtrate obtained due to its hydrophobicity. |
| Millipore MAUF 010 | MultiScreen Ultracel-10 (350 µl) | Activated cellulose 10K NMWL | No filtrate obtained (filter clogged). Pore size too small. |
| Whatman 7700-3307 | UNIFILTER 96 well (350 µl) | Nitrocellulose 0.45 µm | Successful sarin regeneration. However nitrocellulose membrane has low physical strength (brittle). |
| Whatman 7700-2806 | UNIFILTER long drip (800 µl) | PVDF 0.45 µm | Successful sarin regeneration but large amount of bubbling and cross-contamination observed at collection plate after vacuum. Large droplet of filtrate remained at each tip of long drip after filtration. |
| Whatman 7700-1806 | UNIFILTER short drip (800 µl) | PVDF 0.45 µm | No filtrate obtained. Filter exhibit hydrophobic properties even though it is supposed to be hydrophilic. |
| Whatman 7700-3306 [1] | UNIFILTER 96 well (800 µl) short drip | PVDF 0.45 µm | Successful sarin regeneration, but small droplet of filtrate remained at each tip of short drip after filtration. |
| Millipore MSHV N45 [2] | MultiScreen$_{HTS}$ | Hydrophilic Durapore PVDF 0.45 µm | Successful sarin regeneration. No remaining droplet at tip after filtration. |

[1] note that majority of the protocol optimisation results below used the Whatman 7700-3306 as this was initially found to be the best among all the plates (before Millipore MSHV N45 was bought).
[2] Millipore MSHV N45 was selected due to no remaining droplet at tip after filtration and the final protocol optimisation and sarin regeneration LOD were performed using this plate.

TABLE 2

Comparison of various blood volumes for sarin regeneration, showing the downstream volumes of other reagents which in turn affect the filtrate volume available for inhibition on ImmAChE wells.

| Blood Volume | 50 µl | 20 µl | 10 µl |
|---|---|---|---|
| Acetate Buffer + KF Volume | 75 µl | 30 µl | 15 µl |
| Ratio of Acetate buffer:Blood | 1.5:1 | 1.5:1 | 1.5:1 |
| SAS Volume | 350 µl | 140 µl | 70 µl |
| Ratio of SAS:Blood | 7:1 | 7:1 | 7:1 |
| Alumina | 0.45 g | 0.10 g | 0.10 g |
| Total Volume Obtained | 475 µl | 190 µl | 95 µl |
| Filtrate Volume Obtained | <150 µl | <80 µl | <30 µl |
| Filtrate Volume used for Inhibition | 100 µl | 60 µl | N/A |
| % Inhibition of ImmAChE (±SD) | 52.02% (±7.7%) | 67.63% (±0.84%) | N/A | remaining ImmAChE activity. The optimal KF in acetate buffer was determined to be 4.5 volumes, which reactivated the most sarin causing the ImmAChE to be highly inhibited. With VX, the optimal ratio of regeneration buffer to blood was increased slightly to 6.5:1.

5. Regeneration Step Incubation Time

Initial protocols developed for Current test kit Diagnostic Kit for the regeneration step (i.e. blood incubated with acetate buffer containing KF) used 5 minutes incubation for nerve agent regeneration from blood. We investigated the minimal time required for this incubation, so as to attempt to shorten the processing time for the whole diagnosis. We also investigated what effects a longer incubation period (up to 1 hour) may have on the sarin regeneration efficiency, as it may take up to 1 hour for collection of blood samples from 96 individuals (for operating the full plate provided in the diagnostic kit).

Figure 7:
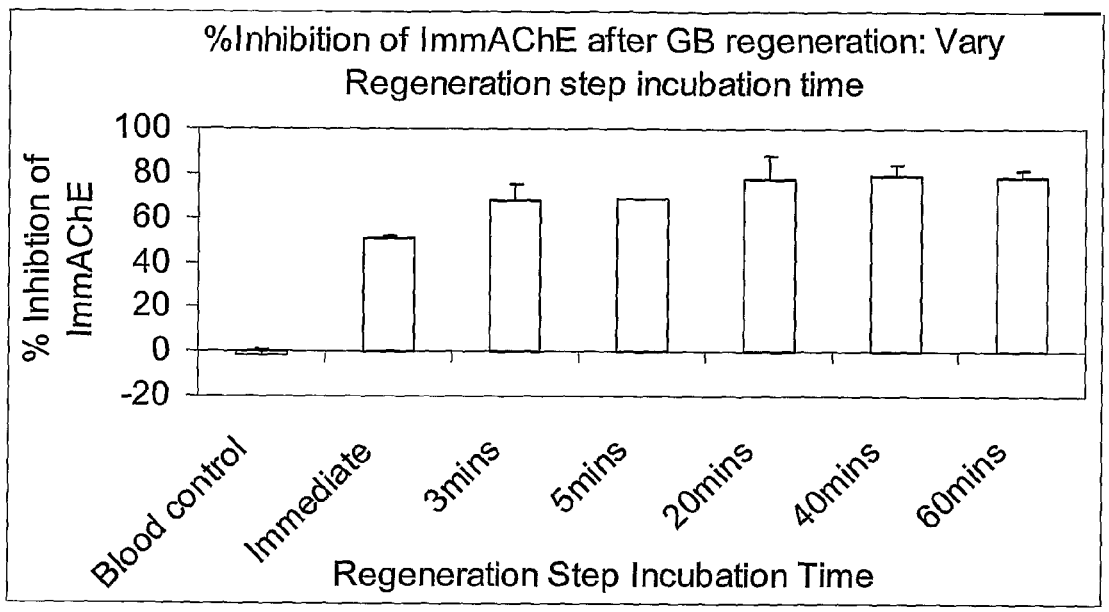
FIG. 7: Detection of Cholinesterase inhibitor over a range of incubation duration during the Reactivation or Regeneration step.

FIG. 7 indicated that the optimal timing was 40 minutes incubation during the regeneration incubation step, which caused the most inhibition of ImmAChE. However, an incubation period of 3-min appeared to be acceptable as well, with only a drop in sensitivity by 11% (78% inhibition versus 67% inhibition for 40 mins and 3 mins incubation respectively). Even without incubation time, there is enough sarin activated to cause about 50% inhibition of ImmAChE plate. Hence, we chose 3 minutes as the minimal time required for incubation, taking into account the importance of the speed of whole assay, versus the maximal sarin regeneration efficiency.

FIG. 7 indicated that a range of various incubation times during Regeneration step (blood with acetate buffer and KF) can be used. Blood spiked with 100 nM sarin was incubated with optimal volume of acetate buffer for various timings up to 1 hr, followed by the general protocol of SAS precipitation, filtration through alumina and inhibition of ImmAChE plate with filtrate for 5 mins. The amount of sarin activated increased with longer incubation periods during regeneration step. Even without incubation, there is enough sarin activated to inhibit about 50% of ImmAChE plate.

6. Amount of Alumina Required

Figure 8:
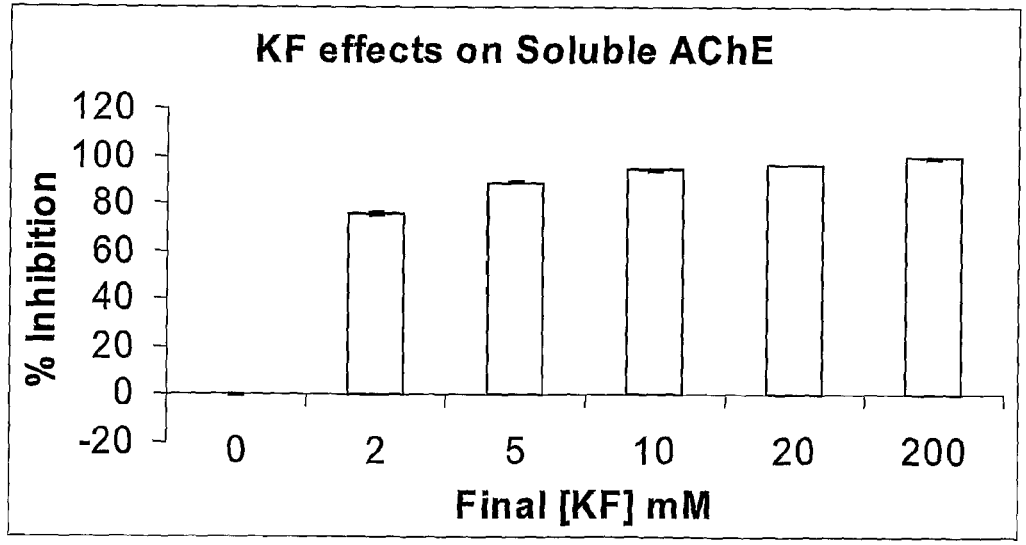
FIG. 8: KF Inhibitory Effects on Acetylcholinesterase Over a Range of Concentration

The regeneration chemical, KF, was determined to have direct inhibitory effects on the test enzyme (FIG. 8). When added at a low concentration of 2 mM KF to acetylcholinesterase (AChE), enzyme activities were observed to decrease by more than 70%. Further increase of KF concentrations to 20 mM results in complete AChE inhibition. To resolve this problem, alumina was used as the complexing agent to remove fluoride ions after the regeneration procedure.

When the blood volume was initially reduced to from 50 µl to 20 µl, the subsequent volumes of acetate buffer and SAS also has to be reduced proportionally. If the original amount of 0.45 g alumina (as used in the protocol for 50 µl blood) was used for 20 µl blood, it would result in very little filtrate obtained due to a large dead volume trapped by the alumina. Hence, we investigated the minimal amount of alumina required to remove the fluoride ions effectively, at the same time reduce the dead volume trapped by large amount of alumina.

The filtration plate was packed with varying amount of alumina (weighed individually and poured into respective well), and sarin-spiked blood mixed with acetate buffer, KF and SAS was filtered through the alumina-packed filtration plate. The ImmAChE wells were then inhibited with the filtrate. Inhibition profile of the effects of varying alumina amount is showed in FIG. 9, with 0.15 g alumina resulting in the maximal inhibition, followed by 0.1 g alumina with a 7% drop in inhibition as compared to 0.15 g. As we were able to obtain a 96-well alumina filler which can fill about 0.125 g/well for the 96 wells at the same time (instead of weighing alumina one by one and pouring into each well which is rather tedious and time-consuming), we decided to use 0.125 g alumina/well as our standard alumina amount.

Figure 9:
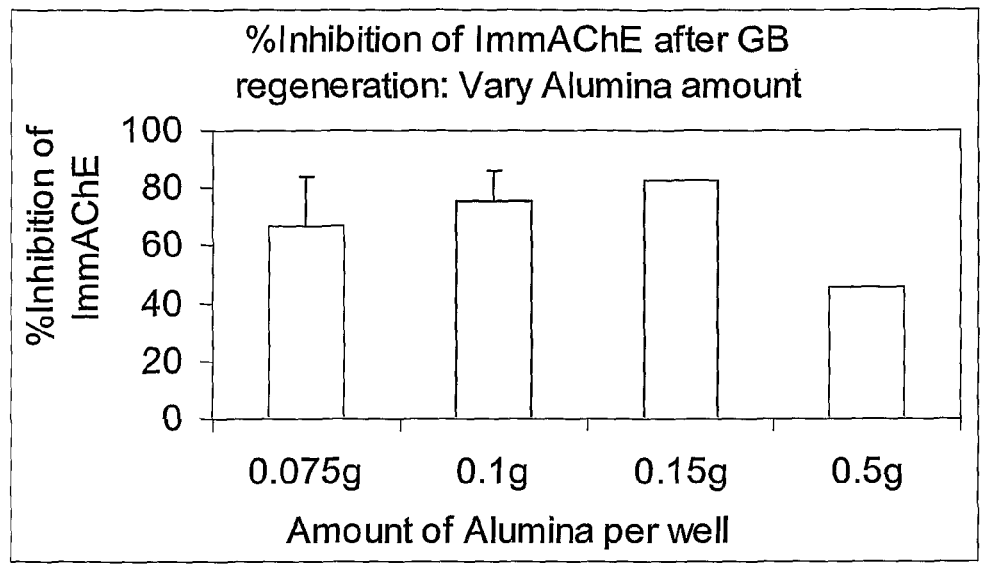
FIG. 9: Detection of Cholinesterase inhibitor using a range of alumina amounts, packed onto the filter.

FIG. 9 demonstrates the range of the amount of alumina packed in filtration plate can be used to detect the sarin regeneration product. Sarin-spiked blood was incubated with KF in acetate buffer, followed by mixing with SAS. The mixture was filtered through filtration plate packed with varying amounts of alumina. Filtrate was incubated with ImmAChE plate to inhibit the ImmAChE for 5 mins, and the remaining amount of ImmAChE was assayed. The optimal amount of alumina was determined to range from 0.1-0.15 g.

7. Minimal Inhibition Time

Figure 10:
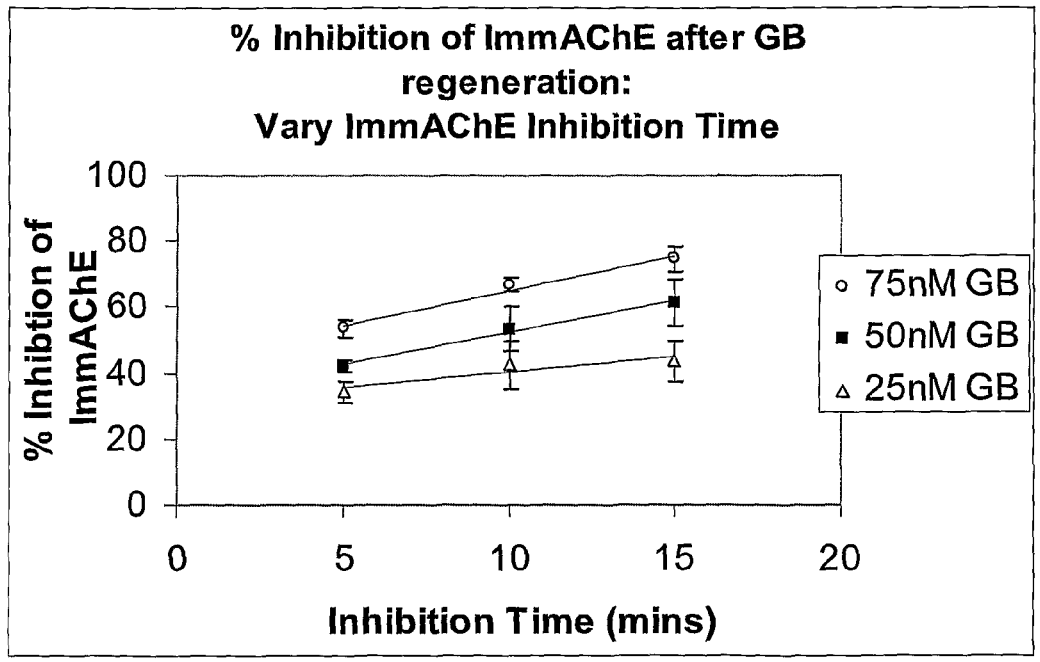
FIG. 10: Detection of Cholinesterase inhibitor over a range of inhibition times with blood samples spiked with 25 nM, 50 nM and 75 nM of cholinesterase inhibitor.

Another critical incubation step in the protocol is the inhibition time of ImmAChE wells with the filtrate. Longer incubation time would theoretically result in greater inhibition. However, we have to balance between the speediness of whole assay versus assay sensitivity. The inhibition time used in the single assay portable system was 10 mins, whereas for the laboratory-based method (where time was not really a constraint), the enzyme inhibition duration was increased to 20 mins instead. Here we investigated the inhibition profile achieved with varying inhibition times and concentrations of spiked sarin in blood samples (FIG. 10). As expected, an increase in inhibition time resulted in proportional increase in inhibition of ImmAChE for all spiked sarin concentrations. With spiked sarin concentration at 25 nM, reducing the inhibition time from 15 mins to 5 mins increased ImmAChE inhibition by 9% while with VX, optimal detection of 10 nM spiked VX was achieved with 15 min inhibition duration. Hence, pending the required sensitivity from the test kit, the operator could select from 5-15 minutes of ImmAChE inhibition duration.

FIG. 10 demonstrates the range of inhibition times of ImmAChE by resultant filtrate (containing activated sarin) before the detection step. Blood spiked with 25 nM, 50 nM and 75 nM sarin was incubated with KF in acetate buffer, followed by mixing with SAS. The mixture was filtered through filtration plate packed with alumina. Filtrate was incubated with ImmAChE plate to inhibit the ImmAChE for 5 mins, 10 mins and 15 mins, and the remaining amount of ImmAChE was assayed. More inhibition was achieved with longer inhibition time, but as a longer time will lengthen the whole assay procedure time, 5 mins inhibition time was selected for a qualitative "Yes/No" answer.

8. Effects of Washing

Figure 11:
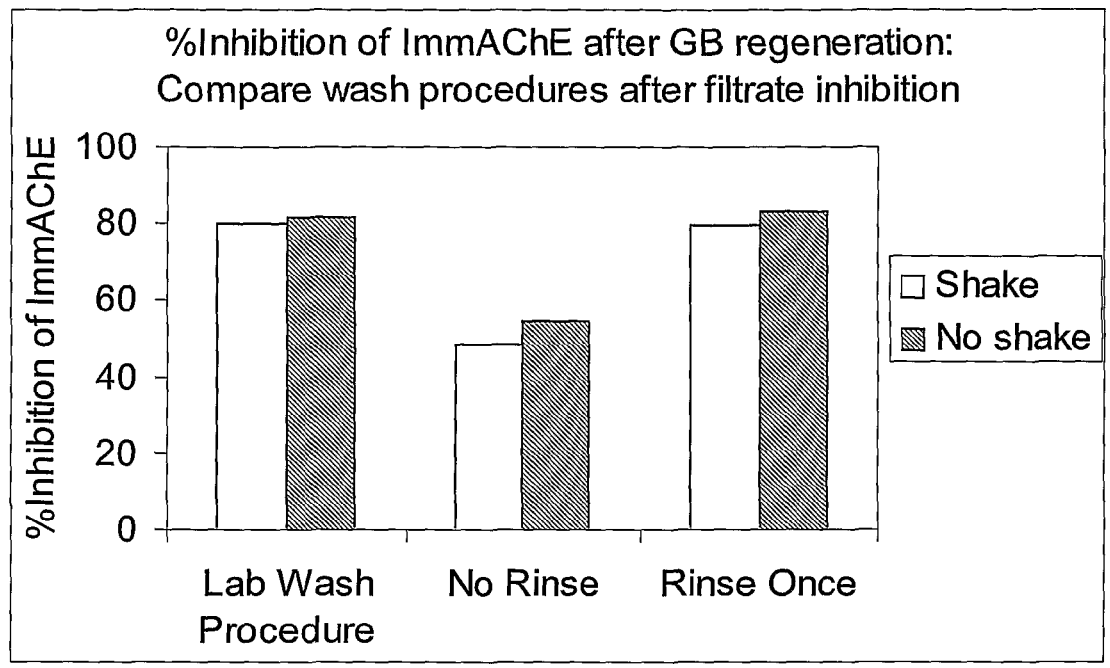
FIG. 11: Detection of Cholinesterase inhibitor using a range of washing procedures on the Immobilised Cholinesterase Enzyme after the inhibition of immobilised cholinesterase by regenerated sarin present in the filtrate.

In the laboratory-based protocol, the ImmAChE plate was washed twice with wash buffer to remove any residual inhibitors, haemoglobin, and other chemicals present that could affect the enzymatic assay. The plate was shaken in an orbital shaker during both the inhibition of ImmAChE with filtrate, and also during the washing steps. In order to attempt to minimise the steps required for the field diagnostic kit, we investigated the effects of omitting the washing step and the shaking step, as it would be very cumbersome to bring an orbital plate shaker into the field. FIG. 11 showed that there was no change in inhibition profile irregardless of whether the ImmAChE plate was washed twice thoroughly with current laboratory protocol, or just rinse once without shaking. However, there was a drastic drop in inhibition when the washing step was totally omitted. This could be due to the remnant low pH of filtrate or the presence of residual blood haemoglobin affecting the enzymatic assay. Thus we concluded that a minimal of 1 rinse step, without the need to shake, is critical for the diagnostic kit protocol.

FIG. 11 compares the washing procedures of ImmAChE after filtrate inhibition step. Blood was spiked with 100 nM sarin, and activated with KF in acetate buffer, followed by addition of SAS and filtration through alumina-packed filter plate. ImmAChE was incubated with filtrate for 15 mins with or without shaking. The conventional laboratory procedure for inhibition and removal of filtrate was a 15 min incubation with shaking on orbital shaker during the inhibition of ImmA-ChE with filtrate, followed by decanting of filtrate, and 2 washes with wash buffer (addition of 200 µl wash buffer per well, decant, another 200 µl wash buffer, shake for 1 min, decant). By omitting the shaking on orbital shaker during the filtrate inhibition step, and the shaking during the rinse procedure, there even a slight increase in the inhibition of ImmAChE. Rinsing once or twice (lab wash procedure) did not affect the inhibition profile, but omitting the rinse step totally resulted in a decrease of inhibition.

9. Components of Wash Buffer

Figure 12:
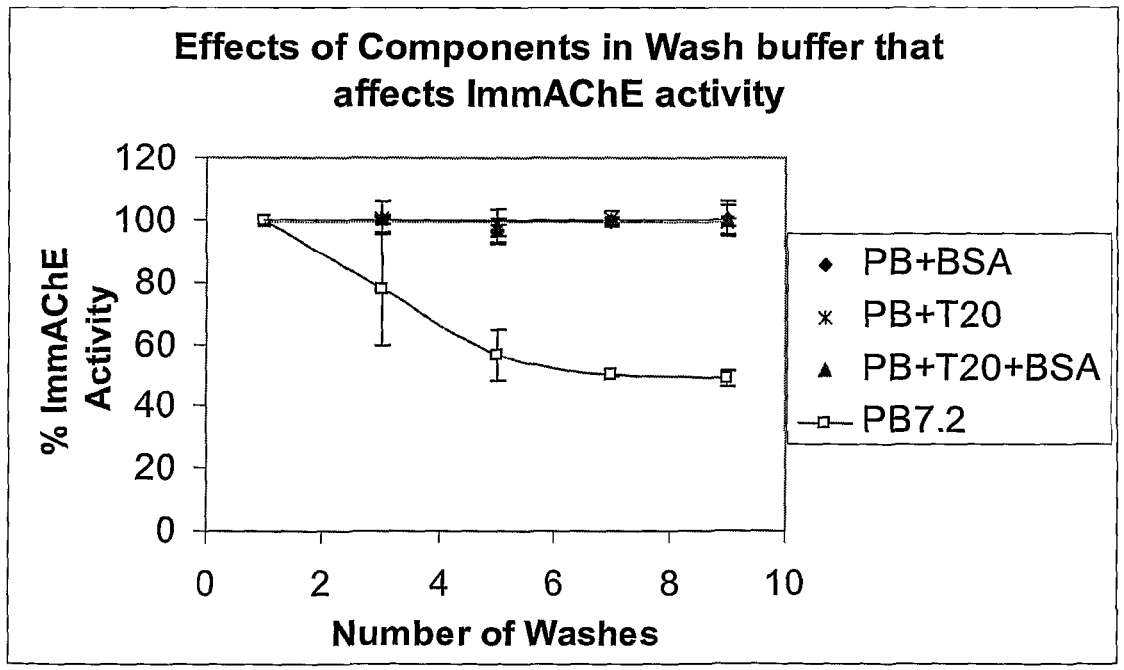
FIG. 12: Effects on Immobilised Cholinesterase Activity by a range of wash buffer components.

During the course of our experiments, we discovered that our $1^{st}$ generation wash buffer 0.1 M phosphate buffer (PB) pH 7.2 caused a steady decrease in ImmAChE activity after each washing step. In order to stabilise the ImmAChE, it was discovered that addition of 0.1% BSA and 0.05% Tween-20 in PB ($2^{nd}$ generation wash buffer) would help to maintain the ImmAChE activity after numerous washing steps. This $2^{nd}$ generation wash buffer was effective in maintaining the ImmAChE activity, such that any decrease in activity would be only attributed to activated nerve agent. However, the presence of BSA meant that the $2^{nd}$ generation wash buffer needs to be kept cold. Hence we investigated whether omitting BSA would have any drastic effects on ImmAChE activity. FIG. 12 showed that the presence of 0.05% Tween-20 alone in PB ($3^{rd}$ generation wash buffer) could help stabilise the ImmAChE, without any drop in activity even after 9 washes. However, with the addition of surfactant Tween-20, there could be bubbles generated in wells during the wash step, and it might be difficult to get rid of the bubbles effectively during the kinetic assay. This may hinder the accuracy of the kinetic results.

FIG. 12 demonstrates the effects of components of wash buffer on the activity of ImmAChE. ImmAChE was washed with 0.1 M Phosphate buffer (PB) pH 7.2 with or without various additives. ImmAChE was washed once prior to assaying with 0.3 mM DTNB and 0.45 mM ASChI (kinetic measurement at 412 nm). After assay, the ImmAChE wells were washed twice with various buffers. The ImmAChE were assayed a total of 5 times, with 2 washes in between each assay. Addition of 0.05% Tween 20 and/or 0.1% BSA helped to stabilise the ImmAChE during the washing procedure, whereas washing with PB without any additives resulted in 50% decrease in ImmAChE activity after 5 assays.

10. SAS Precipitation Step Incubation Time

Figure 13:
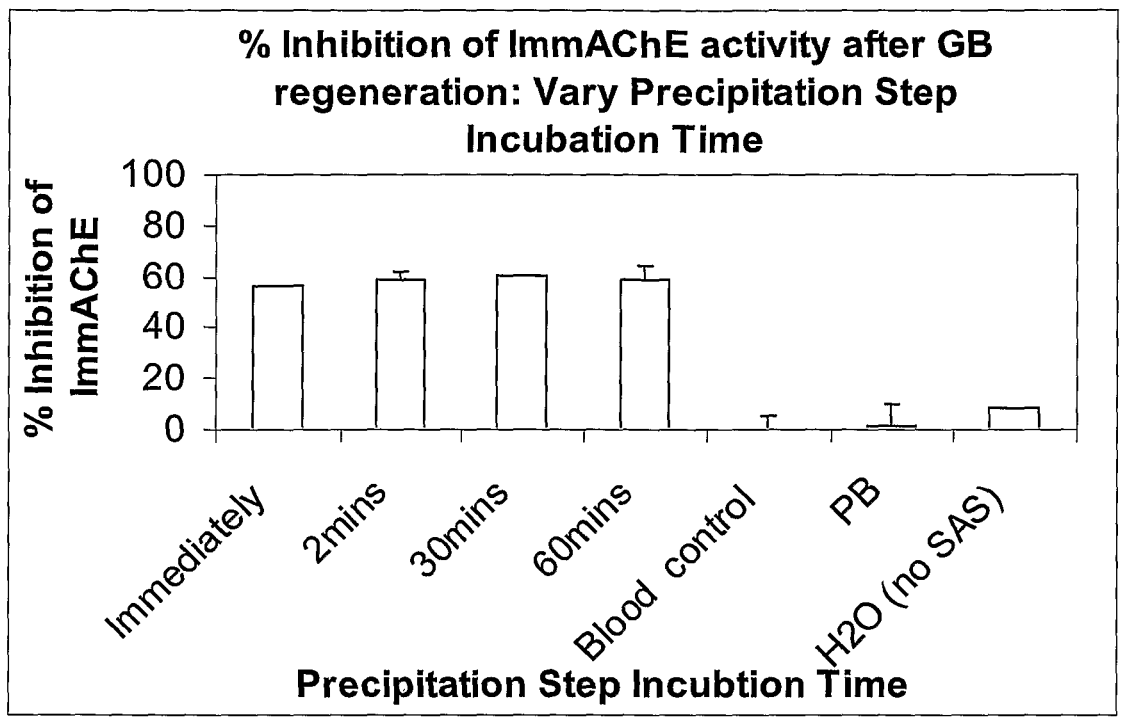
FIG. 13: Detection of Cholinesterase inhibitor over a range of incubation duration during the blood protein precipitation step.
Figure 14:
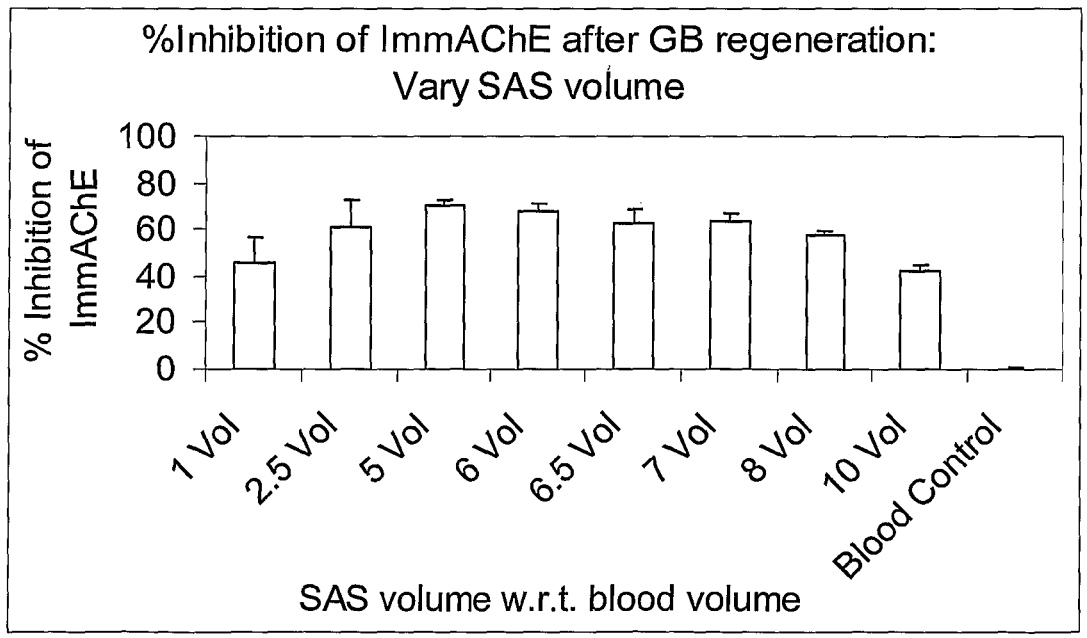
FIG. 14: Detection of Cholinesterase inhibitor over a range of varying ratio of Saturated Ammonium Sulphate (SAS) volume to blood sample volume and filtered with alumina-packed Whatman 7700-3306 filtration plates.
Figure 15:
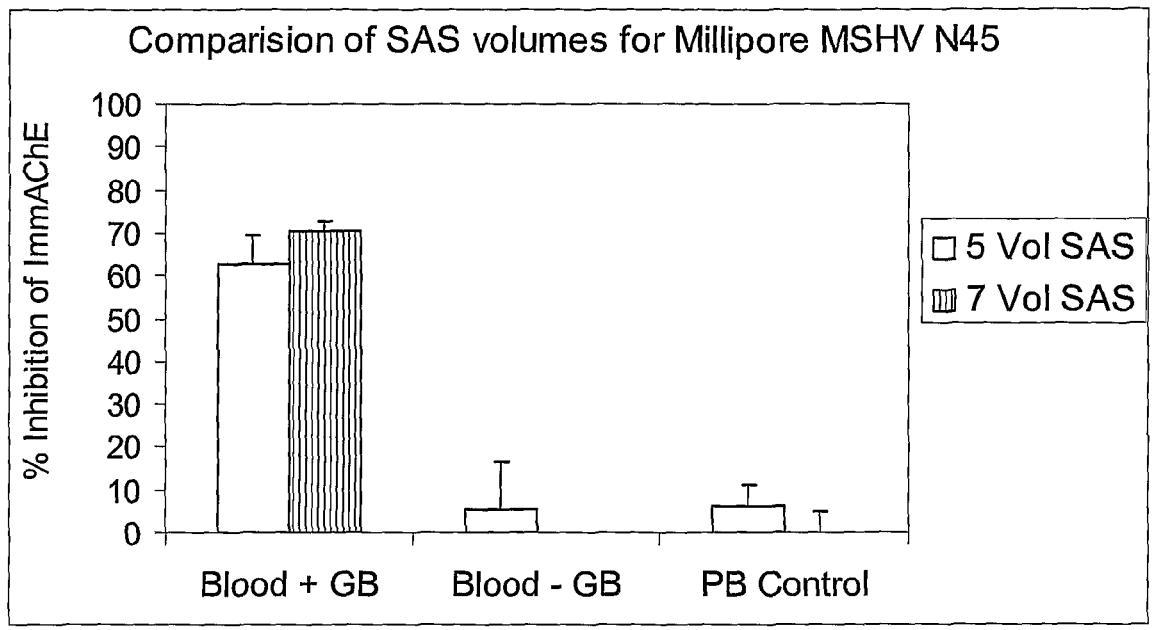
FIG. 15: Detection of Cholinesterase inhibitor at a varying ratio of SAS volume to blood volume and filtered through alumina and an inert hydrophilic membrane filter in this case a Millipore MSHV N45 filtration plate.
Figure 16:
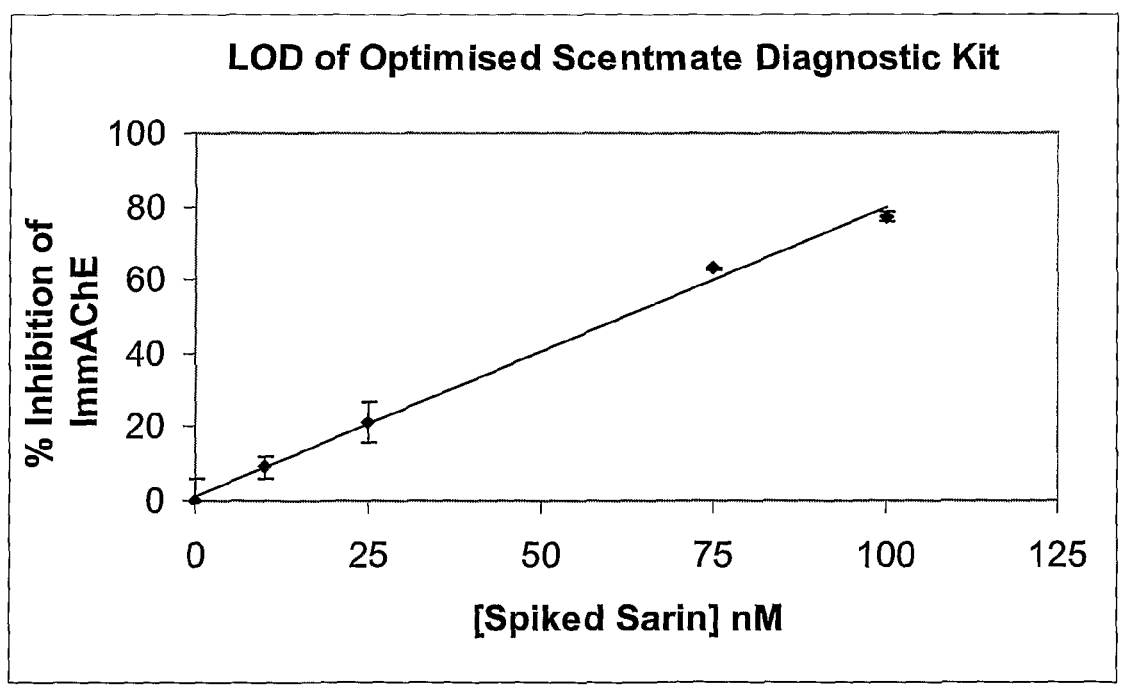
FIG. 16: Limit of detection (LOD) of the Cholinesterase inhibitor Sarin at a range of concentrations of cholinesterase inhibitor spiked into blood samples using an exemplary kit.

We investigated the minimal time required for incubation of SAS with the acidified blood and KF to achieve effective precipitation of endogenous blood proteins, which is essential for the success of sarin regeneration protocol. From FIG. 13, there was not much improvement in inhibition whether the mixture was incubated for 2 mins to 1 hour, or filtered immediately without incubation. Hence we concluded that no incubation is required for this step. Moreover, if there is any delay (tested up to 1 hour) during transfer of mixture to filtration plate, this will not compromise on the detection sensitivity of the diagnostic kit.

FIG. 13 demonstrated the effects of varying incubation time during the precipitation step (SAS incubation with acidified blood). Sarin-spiked blood was incubated for 3 mins with acetate buffer and KF, followed by addition of 7×volumes of SAS. The mixture was then filtered through alumina-packed filtration plate immediately, or after 2 mins, 30 mins or 1 hr incubation. ImmAChE plate was inhibited with filtrate for 5 mins and assayed for inhibition of ImmAChE. Enough sarin was activated to inhibit ImmAChE, irregardless of incubation time. When water was used in place of SAS, minimal inhibition of ImmAChE occurred, indicating that SAS is an important step in the regeneration protocol.

Removal of endogenous blood proteins is an important step to ensure the success of downstream inhibition of ImmAChE wells. When water was used in place of SAS, minimal inhibition of ImmAChE occurred, indicating that SAS is an important step in the regeneration protocol.

11. Volume of SAS to Blood Ratio

In the original diagnostic kit protocol, the SAS volume was relatively large (10 to 12 volumes of blood) in order to achieve a final ammonium sulphate concentration of 80% during the precipitation step. However, more SAS volume meant that any sarin that was activated would be greatly diluted by the large SAS volume. Therefore, we also investigated the ratio of SAS to blood volume and found that a lesser amount of SAS was more effective in achieving a higher degree of inhibition on ImmAChE wells. For this experiment, the optimal SAS was 5 volumes that of blood volume (FIG. 14) when Whatman 7700-3306 filtration plate was used. We re-optimised the SAS volume with the new Millipore MSHV N45 filtration plate and found that the optimal ratio of SAS to blood volume was 7:1 instead of 5:1, which was selected for the final diagnostic kit protocol (FIG. 15).

FIG. 14 demonstrates the effects of varying SAS to blood ratio on sarin regeneration efficiency. Sarin-spiked blood was reacted with KF in acetate buffer, followed by addition of various volumes of SAS, 20 μl to 200 μl (corresponding to 1 volume to 10 volumes w.r.t. blood volume). Resultant mixture was clean up with alumina-packed filtration plate (Whatman 7700-3306) and filtrate was used to inhibit ImmAChE on plate. The optimal ratio of SAS to blood is 5:1, with the maximum ImmAChE inhibition.

FIG. 15 is a comparison of ratio of SAS to blood volume for new Millipore MSHV N45 filtration plate. Sarin-spiked blood was reacted with KF in acetate buffer, followed by addition of either 5 or 7 volumes of SAS w.r.t. blood volume, corresponding to 100 μl or 140 μl respectively. Resultant mixture was clean up with alumina-packed filtration plate (Millipore MSHV N45) and filtrate was used to inhibit ImmAChE on plate. The optimal ratio of SAS to blood is 7:1, with the maximum ImmAChE inhibition.

Influence of Shuffling Fluoride Removal and Blood Protein Precipitation Steps

The order of fluoride removal by alumina and blood protein precipitation by SAS in the Current test kit Protocol has an important influence in the resulting sensitivity of the diagnostic method for detection of regenerated or reactivated nerve enzyme inhibitors. Placing the fluoride removal step ahead of the blood protein precipitation and removal step decreased inhibition of immobilised cholinesterase in Current test kit Kit by about 70% with a 100 nM Spiked Sarin Blood Sample (Table 3). This decrement in diagnostic sensitivity is likely to be related to re-inhibition of blood proteins by the regenerated nerve enzyme inhibitors once fluoride ions are chelated out of the system. The latter step also effectively prevented further reactivation of the cholinesterase-inhibitor complex. On the other hand, if blood proteins are first precipitated out of solution, this re-inhibition process could not take place upon subsequent removal of fluoride ions.

TABLE 3

Decrement in Current test kit Sensitivity as Indicated by Reduced % Inhibition of ImmAChE With Reshuffled Current test kit Protocol Where Fluoride Removal is Executed Prior Blood Protein Precipitation

| | % Inhibition of ImmAChE Observed | | |
| --- | --- | --- | --- |
| | 100 nM Spiked Sarin in Blood Sample | 50 nM Spiked Sarin in Blood Sample | 20 nM Spiked Sarin in Blood Sample |
| Normal Current test kit Protocol | 80% | Not Conducted | 40% |
| Reshuffled Current test kit Protocol | 13% | 7% | Not Conducted |

The finalised exemplary protocols that contribute to the ability of the rapid current test diagnostic kit thus include:
  i. Briefly rinse Immobilised Acetylcholinesterase (AChE) Plate to remove any protective trehalose-albumin layers stabilising the immobilised AChE
  ii. Addition of substrate and chromogen to Immobilised Acetylcholinesterase (AChE) plate and assay for 2 min to determine initial activity.
  iii. Concurrently, add potassium fluoride solution to blood (20 ul) acidified by acetate buffer to regenerate acetylcholinesterase inhibitor as a fluorinated analog (eg. Sarin). Regeneration process is allowed to progress for about 3-5 min. Optimal acetate buffer to blood ratio varies from 4.5:1 to 6.5:1, depending on the nerve enzyme inhibitors involved.

iv. Removal of endogenous blood proteins by addition of about 140 μl of saturated ammonium sulfate to prevent reactivated nerve agent from re-binding to blood cholinesterases (total dilution factor is 12.5 fold). It is vital to perform this step prior fluoride ion removal as sensitivity of method for nerve enzyme inhibitor will be significantly reduced if fluoride ion removal is carried out prior precipitation of blood proteins.

v. Removal of fluoride ions from mixture by passage through a Millipore PVDF filtration plate packed with alumina. This step is crucial as free fluoride ions can inhibit as well as interfere with nerve agent or pesticide inhibition of Immobilised AChE.

vi. Inhibition of Immobilised AChE with reactivated nerve agent found in resultant mixture from step (iii) for 5-15 min vii. Brief washing of Immobilised AChE to remove any residual mixture after inhibition. Washed solution should contain a surfactant for e.g. Tween-20 to prevent any decrement in activity of Immobilised AChE induced by the washing process viii. Addition of substrate ASChI (0.45 mM) and chromogen DTNB (0.3 mM) for ImmAChE, followed by kinetic assay at 412 nm for 2 min to determine remaining activity and hence % inhibition of ImmAChE In Vitro Human Blood Experiments: Measurement of Blood Acetylcholinesterase Inhibition and Current Test Response with Addition of Sarin, VX, Tabun or Dichlorvos A. Determination of Threshold Value for Non-Specific Inhibition of Immobilised AChE by Normal Blood Samples In order to determine the true detection window of this diagnostic kit, it is important to know the threshold value of the degree of non-specific inhibition of ImmAChE wells caused by just normal blood samples (without any nerve agents). Blood samples were taken from 5 volunteers and used as controls in nerve agent regeneration protocol, and run in duplicates for 2 consecutive days. The highest inhibition was 5.4% for one reading of an individual (Table 4). However, due to the small sampling size of normal blood controls (without ethics committee approval), we decided to take the threshold value of non-specific inhibition to be the additive value of mean inhibition and 10 times of standard deviation, which is 17.28% inhibition. This threshold value could be better adjusted once a sufficient sampling size of normal individuals is obtained.

TABLE 4

Threshold value of non-specific inhibition of ImmAChE obtained from blood samples of 5 normal individuals.

| Blood Sample | Day 1 (% Inhibition of ImmAChE) | Day 2 (% Inhibition of ImmAChE) |
|---|---|---|
| Normal Person 1 | 2.8 | 0.0 |
| | 4.0 | 3.8 |
| Normal Person 2 | 3.5 | 2.7 |
| | 4.2 | 2.5 |
| Normal Person 3 | 3.3 | 2.2 |
| | 4.2 | 3.1 |
| Normal Person 4 | 4.4 | 5.4 |
| | 5.4 | 4.0 |
| Normal Person 5 | 4.8 | 2.2 |
| | 5.3 | 1.6 |
| Mean of 5 normal blood samples | | 3.48% |
| Standard Deviation (STDev) of 5 samples | | 1.38% |
| 10 × STDev | | 13.80% |
| Threshold value for non-specific inhibition (Mean + 10 SD) | | 17.28% |

B. Determining Limits of Detection (LOD) of Current Test Diagnostic Kit

With the final optimised protocol, the detection sensitivity of the Current test diagnostic kit was tested with various concentrations of sarin spiked in human blood. With the use of sarin calibration standards on the immobilisation plate, we determined the mean level of activated sarin from spiked blood samples to be 67.5% of the initial spiked and diluted (12.5×) amount. From FIG. 16 and Table 5, the Current test diagnostic kit's LOD for Sarin was determined to 20 nM of sarin spiked into blood, taking into account the diagnostic kit's threshold value of 17.28% for non-specific inhibition. This corresponded with a detected level of 1.472 nM of regenerated sarin from the blood sample.

From van der Schans study of asymptomatic sarin exposure on rhesus monkeys, the concentration of reactivated sarin determined from the blood samples on the day of exposure was 20.7 nM (Marcel J. van der Schans, et. al. Retrospective detection of exposure to nerve agents: analysis of phosphofluoridates originating from fluoride-induced reactivation of phosphylated BuChE. *Archives of Toxicology* 2004; 78: 508-524). By direct extrapolation of our in vitro results, it does suggest that Current test diagnostic kit should be able to detect asymptomatic exposure to sarin in primates and hence in human. This extrapolation will be confirmed with further studies.

TABLE 5

Current Test Kit Detector Response With Various Spiked Sarin Amounts Into Human Blood

| Spiked Sarin in Blood (nM) | % of Blood AChE Inhibition | % Current test Kit Response | Estimated $[Sarin]_{activated}$ Detected (nM) |
|---|---|---|---|
| 0 | 0.0 | 0.0 | 0.0 |
| 10 | 12.2 | 14.7 | 0.5 |
| 15 | 18.0 | 21.3 | 0.8 |

TABLE 5-continued Current Test Kit Detector Response With Various
Spiked Sarin Amounts Into Human Blood

| Spiked Sarin in Blood (nM) | % of Blood AChE Inhibition | % Current test Kit Response | Estimated [Sarin]$_{activated}$ Detected (nM) |
|---|---|---|---|
| 20 | 22.9 | 26.5 | 1.5 |
| 35 | 36.9 | 40.6 | 1.9 |
| 50 | 48.0 | 51.1 | 2.7 |
| 60 | 54.6 | 57.0 | 3.2 |
| 75 | 62.9 | 64.2 | 4.1 |
| 100 | 74.1 | 74.0 | 5.4 |

Figures 17, 18:
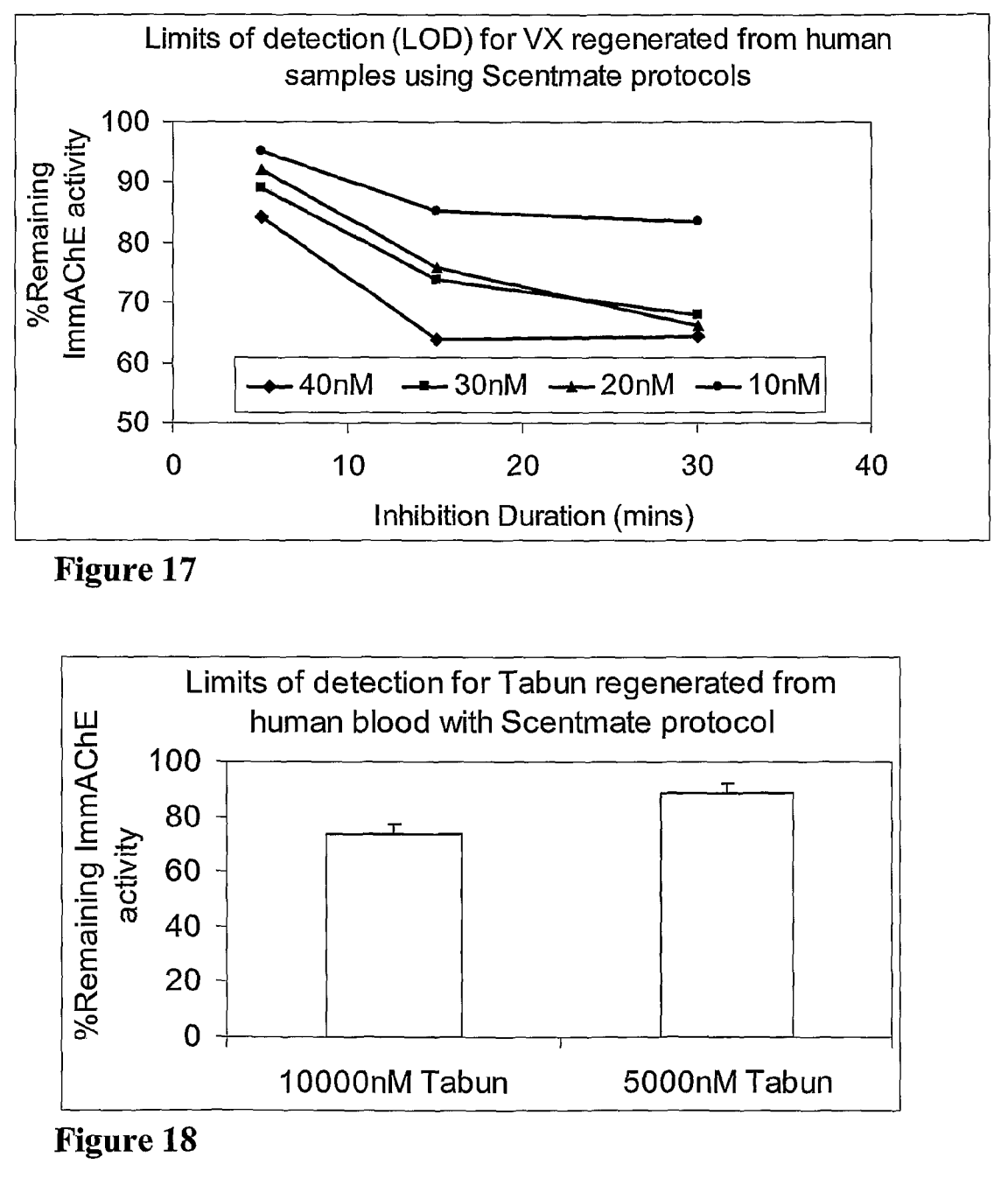
Figure 19:
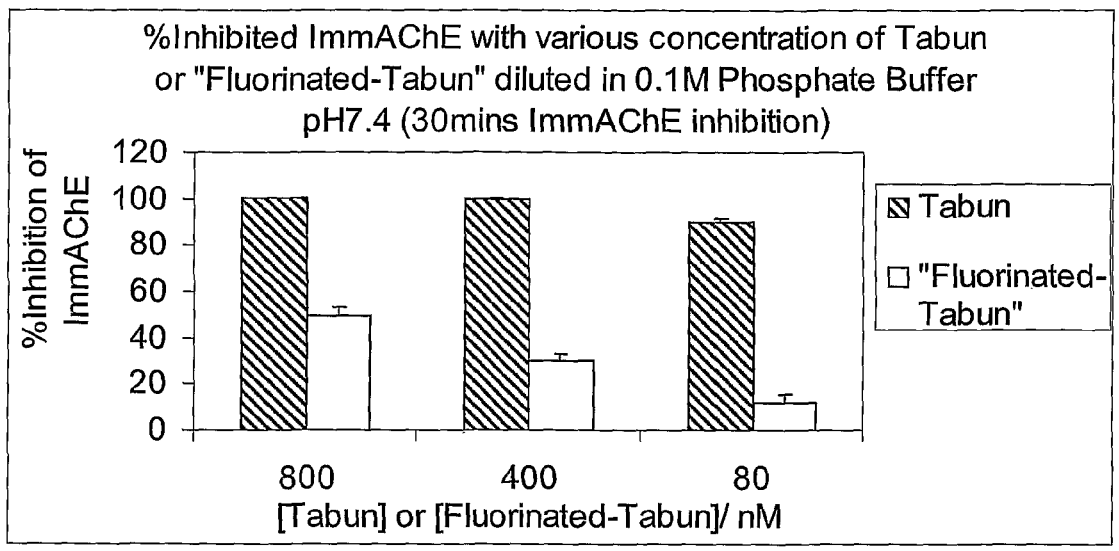
FIG. 19: Differential ImmAChE inhibitory effects Between "Fluorinated-Tabun" and Tabun.
Figure 20:
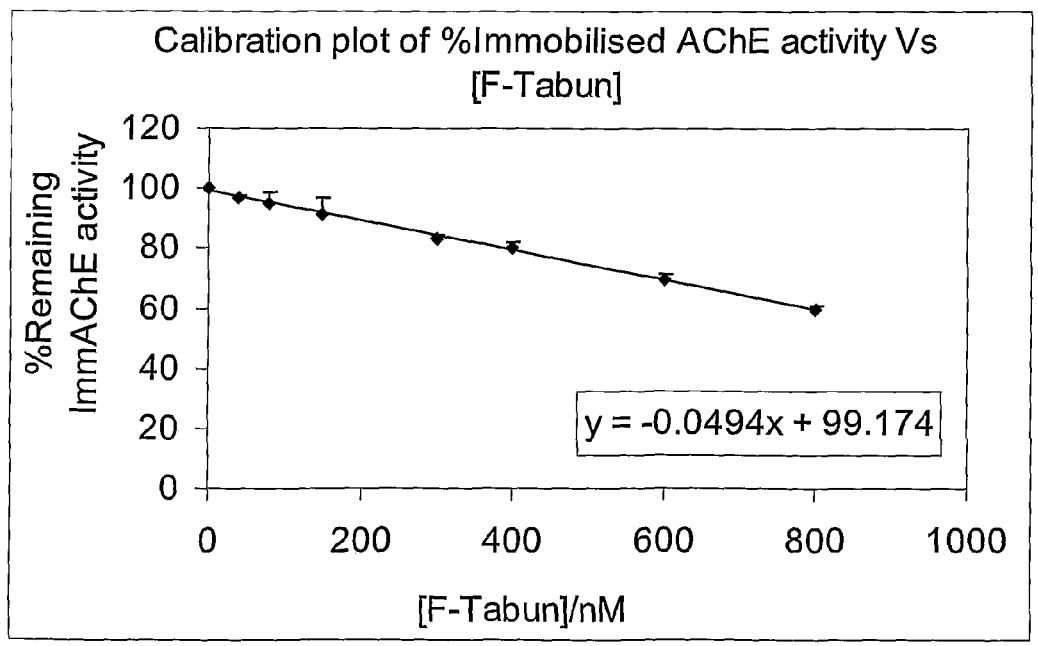
FIG. 20: Calibration Plot of % Immobilised AChE Activity vs [Fluorinated Tabun]

With VX (FIG. 17) and Tabun (FIG. 18), the respective LOD determined was 10 nM and 10,000 nM spiked concentrations respectively. The Current test kit diagnostic protocol is less sensitive to Tabun primarily because the fluorinated version of Tabun is not a strong cholinesterase inhibitor (FIG. 19). Based on the % remaining Immobilised AChE activity (i.e., 73%; FIG. 18) observed with 10,000 nM of spiked Tabun, using the calibration plot of % ImmAChE Activity vs Concentration of Fluorinated Tabun (FIG. 20), the estimated concentration of Fluorinated Tabun present in the Current test kit filtrate would be 530 nM. This is close to the required level of fluorinated Tabun for 20% inhibition of Immobilised AChE (FIG. 19).

Figure 21:
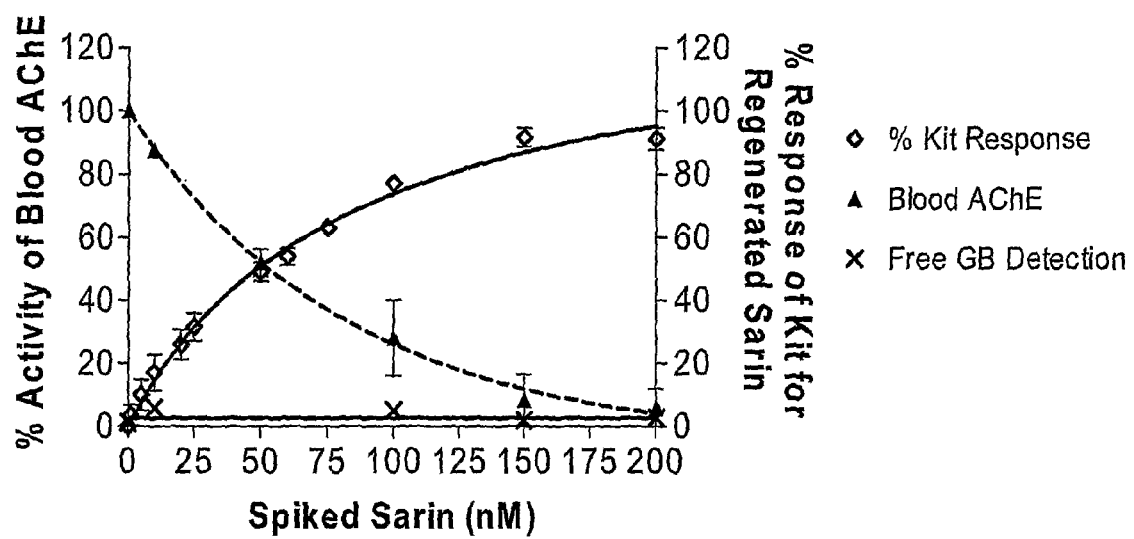
FIG. 21: Sensitivity of cholinesterase inhibitor detection using an exemplary kit to detect a range of concentrations of cholinesterase inhibitor spiked into blood samples in comparison with conventional kits for measuring a decline in cholinesterase enzyme in a blood sample.

The relevance of Current test detection capability could be related to conventional blood acetylcholinesterase (AChE) assay technique for diagnosis of OP poisoning (FIG. 21). Compared to conventional blood AChE assay where a minimum of 30% activity depreciation from baseline is required for initial suspicion of prior OP exposure (Table 5), the current Current test kit kit could confirm OP exposure when blood acetylcholinesterase depreciation is less than 30% of normal. This data thus indicates that Current test would assist in rapid triage of suspected casualties beyond what is afforded by conventional Blood AChE Assay capability.

The current Current test kit kit has also been validated with Dichlorvos (OP pesticide; Table 6). The residual activity of blood AChE of dichlorvos-spiked blood samples were monitored with commercially-available AChE assay kit for comparison. Inhibition of blood AChE was monitored with a commercial AChE Assay Kit. A positive signal of 22% was obtained using Current test at 1000 nM Dichlorvos spiked in blood, whereas a possible indication of pesticide poisoning monitored by >30% blood AChE inhibition occurs at a higher spiking concentration of 1250 nM Dichlorvos. Similar to what was observed for sarin nerve gas, Current test kit test kit was also able to diagnose Dichlorvos exposure when % Blood AChE inhibition was less than 30%.

TABLE 6

Percentage Inhibition Of Blood AChE Versus Current
Test Kit Response With Various Dichlorvos Amounts.

| Spiked Dichlorvos in Blood (nM) | % Inhibition of Blood AChE | % Current test Kit Response |
|---|---|---|
| 0 | 0.0 | 0.0 |
| 1000 | 26.6 | 22.7 |
| 1250 | 33.0 | 30.4 |
| 1500 | 35.0 | 39.8 |

Validation Current Test Kit Test Protocol to an Asymptomatic Challenge of Sarin in a Laboratory Rat Model None of the 3 challenged rats displayed any signs or manifestations of nerve agent exposure post-sarin challenge. They returned to their habitual grooming and feeding when returned to their home cages. While traces of free sarin could not be detected in the rat's blood, application of Current test kit Protocol on rat blood collected ½ h post sarin exposure indicated a significant presence of regenerated sarin from the blood sample (Table 7). Detection of regenerated sarin was achieved up to 4 h post Sarin administration

TABLE 7

Tabulation of Free and Regenerated Sarin Recovered
from Sprague Dawley Rats (n = 3) Administered with
0.4xLD$_{50}$ Dose of Sarin Subcutaneously

| Blood drawn time point Post-Sarin (h) | % Inhibition of Immobilised Cholinesterase Sarin Regenerated from Rat Blood by Current test kit Protocol | % Inhibition of Immobilised Cholinesterase by Free Sarin Present in Rat Blood |
|---|---|---|
| 0 | 0 | 0 |
| 0.5 | 47 | 0 |
| 1 | 51 | 0 |
| 1.5 | 34 | 0 |
| 2 | 32 | 0 |
| 2.5 | 25 | 0 |
| 3.5 | 17 | 0 |
| 4 | 13 | 0 |

Determining Current Test Response to Sarin in Human Blood Samples in the Presence of Pyridostigmine and Oxime Reactivator, 2-Pralidoxime Chloride Pyridostigmine Bromide (Pyr) is a prophylactic compound often given to soldiers and emergency personnel who are going to enter an area where there are suspected cholinesterase inhibitors particularly nerve gases.

Similarly Pyridine-2-aldoxime methochloride (2PAM) is an oxime treatment often given to individuals who are suspected to have been exposed to a cholinesterase inhibitor.

It is assumed that:
Pyr concentration in blood where "1 E-07M Pyr in human blood after oral administration of 30-60 mg, when neither metabolic excretion nor conversion was considered"
2PAM concentration in blood where "600 mg autoinjector (Mark I) should give Cmax of 6.5 µg/ml (38 µM)"

FIGS. 22 and 23 demonstrate that it is still possible to detect an individual's exposure to a cholinesterase inhibitor even if they were given a prophylactic compound before the possible exposure took place or a treatment after suspected exposure.

Figure 22A:
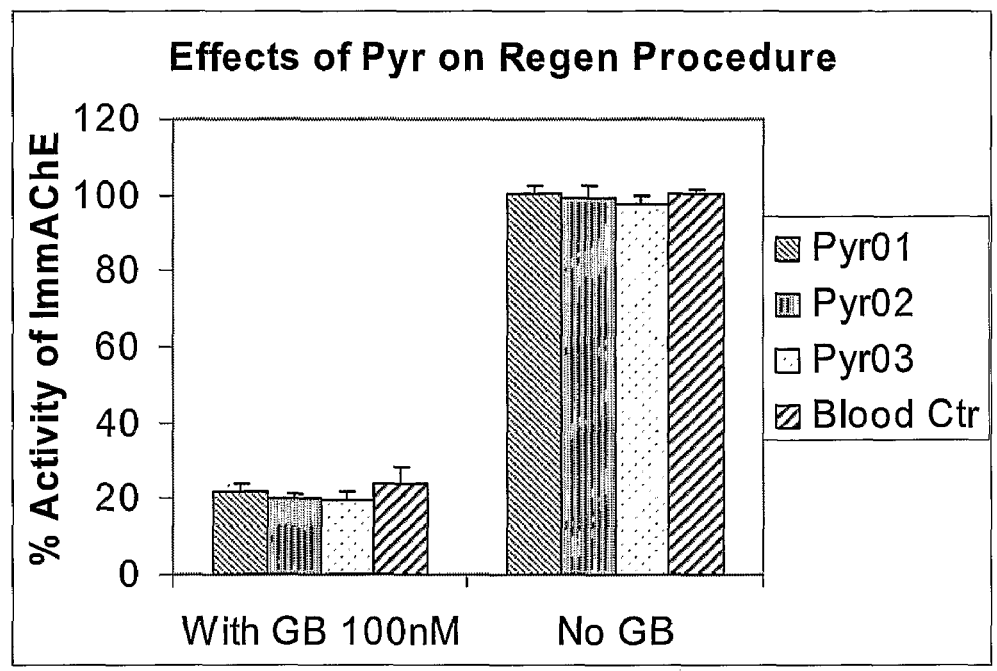
FIG. 22 A & B: The effect of a prophylactic drug on the detection of a cholinesterase inhibitor with the method of the invention. The prophylactic drug is added to a sample before possible exposure to a cholinesterase inhibitor.
Figure 22B:
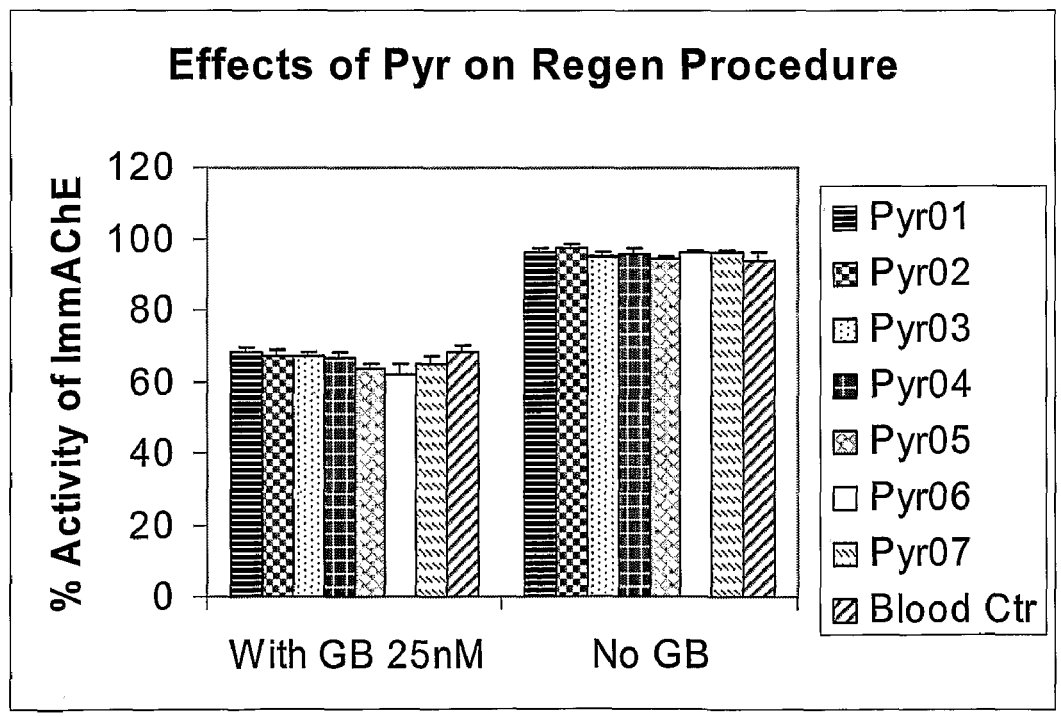

Pyridostigmine Data:
Even where a high dose of the prophylactic Pyridostigmine is used, the presence of a cholinesterase inhibitor is detected (FIG. 22). Pyr is added to blood prior to spiking with either 100 nM sarin (FIG. 22A) or 25 nM sarin (FIG. 22B), to simulate that Pyr, a prophylactic drug, is given before nerve agent exposure.

Figure 23A:
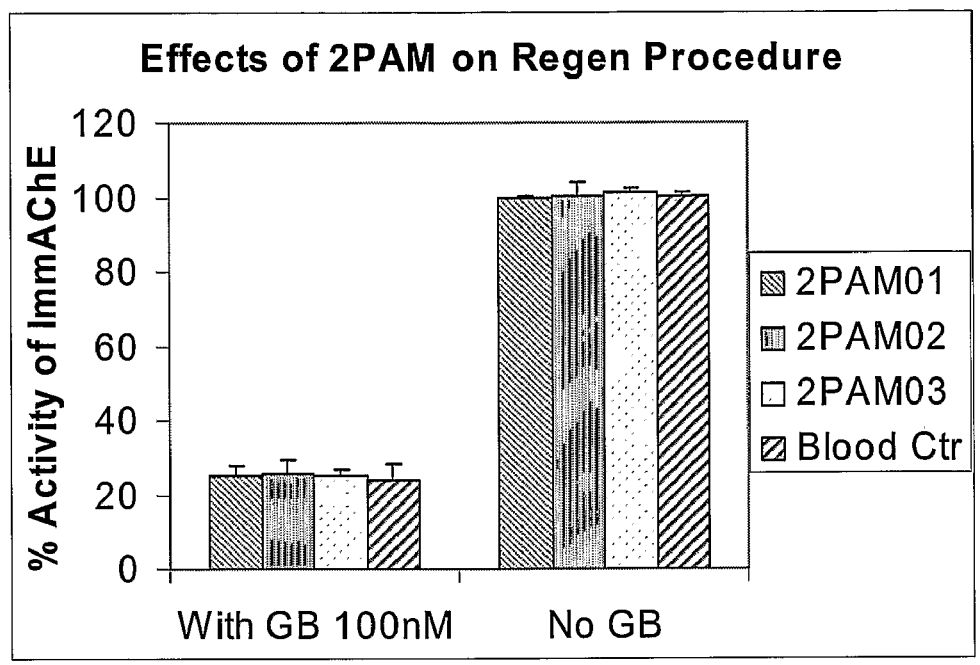
FIG. 23 A & B: The effect of a treatment drug on detection of a cholinesterase inhibitor with the method of the invention. The treatment drug is added to a sample after possible exposure to a cholinesterase inhibitor.
Figure 23B:
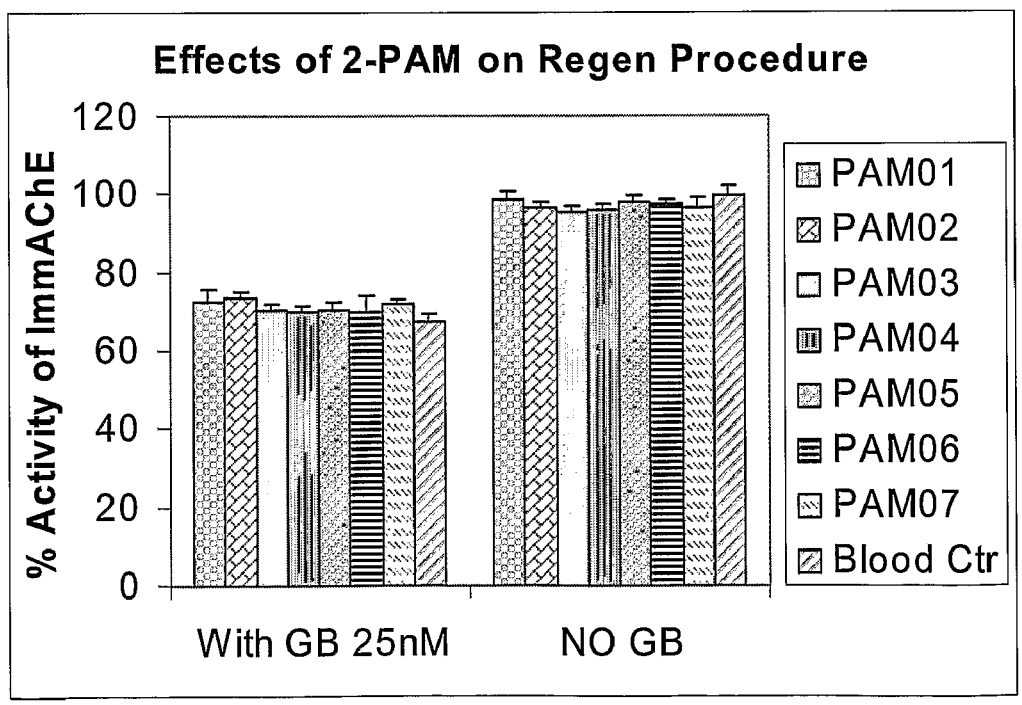

2-PAM Data:
Even when a high dose of the treatment 2-PAM is used, the presence of a cholinesterase inhibitor is detected (FIG. 23). Either 100 nM Sarin (FIG. 23A) or 25 nM sarin (FIG. 23B) is spiked in blood for about 30 mins before 2PAM is added to stimulate a treatment dose. 2-PAM is added to blood after spiking with sarin, to simulate that 2Pam, a treatment drug, is given after suspected exposure to a cholinesterase inhibitor.

Once nerve agent antidotes have been administered to suspected casualties of nerve agent exposure, it is difficult to rely on clinical symptoms for a confirmatory diagnosis of actual nerve agent exposure. This is especially so for mild to moderate cases of nerve agent exposure. Having the ability to ascertain post antidotes administration, whether observed clinical symptoms of discomfort or malaise arose from actual nerve agent exposure or from the administered antidotes would assist the physicians in their therapeutic actions. There are also new clinical reports that oxime therapy should be continued as long as there are reactivatable cholinesterases within the body. The Current Current test kit diagnostic device would provide this answer as continued presence of recoverable nerve agents from blood samples would indicate the presence of reactivatable cholinesterases.

nM of spiked Sarin concentration in human blood, the maximum theoretical Sarin concentration in the Current test kit Filtrate (obtained from Step a) would be (1.68±0.1) nM (Table 9). Through linear regression analysis of Cholinesterase Inhibition Plot, we determined that (1.47±0.4) nM of Sarin (Table 10) was present in the Current test kit Filtrate Sample used in Step (b) of Current test kit Protocol for Inhibiting Immobilised Cholinesterase. Hence, as both figures are not significantly different, the alternate analytical procedure using solid phase extraction followed by GCMS analysis has validated the accuracy of the Current test kit protocol for determining regenerated Sarin. These results also affirmed that all inhibitory activities on the immobilised cholinesterase of Current test kit Kit arose primarily from the regenerated Sarin.

TABLE 8

Tabulation of Recovery Factors For SPE Extraction, Detected Concentration of Regenerated Sarin in Current test kit Filtrate and Correlation Factor Between Analysed and Estimated Actual Sarin Concentration in Filtrate

| Sample description | Recovery of GB in 20 ml filtrate (%), with concentration factor of 20 | Concentration detected in Current test kit Filtrate by SPE (nM) | Estimate "Actual" Conc in Current test kit Filtrate Corrected for SPE Losses (nM) | Final Sarin Concentration Spiked In Blood (nM) | Correlation Factor |
|---|---|---|---|---|---|
| Blood + Ac + KF + Sarin, spin & filter thru alumina | 40.90 | 3.27 | 8.87 | 100 | 0.089 |
| | 35.41 | 2.83 | 7.68 | 100 | 0.077 |
| | 40.05 | 3.20 | 8.69 | 100 | 0.087 |
| Phosphate buffer + Sarin | 36.87 | 2.95 | 8.00 | 100 | NA |

Validating Identity of Activated Agent Using Current Test Technology

Sarin is identifiable on GCMS by both its retention time (7±0.5 min) and mass spectrometry data (m/z 125, 99 and 81). To confirm the identity of the inhibitory compound obtained from Step (a) of Current test kit Protocol, which involved fluoride reactivation, blood proteins precipitation and alumina-aided removal of fluoride ions, the filtrate was subjected to solid phase extraction and the ethyl acetate eluant further analysed by GCMS (EI-SIM) mode. From the similar GC-MS chromatograms of Standard Sarin (FIG. 24A) vs regenerated inhibitor from human blood (FIG. 24B), solid phase extracts of filtrate obtained from sarin-spiked blood samples using Current test kit Protocol is determined to contain sarin nerve agent.

Validating Accuracy of Current Test Kit Protocol in Determining Amount of Regenerated Nerve Agent Inhibitors Using Alternate SPE-GCMS Analytical Technique A linear calibration plot (FIG. 25) for Sarin was obtainable using GCMS analysis of sarin prepared in ethyl acetate solutions. As the lowest quantifiable limit for Sarin with GCMS was 2 parts per billion (ppb) or 14 nM, a 20-fold concentration step was effected at the solid phase recovery process. From recovery studies conducted on phosphate buffer spiked with Sarin samples, C18-solid phase extraction (SPE) cartridges provided a mean recovery of 36.87% of initial spiked Sarin (Table 8). Similar recovery factors were observed for regenerated sarin recovered from human blood samples, after being processed by the Sample Regeneration and Precipitation protocols (Step a) in Current test kit Procedure. Correcting for losses by the SPE process, we determined that for an initial 20

TABLE 9

Estimated Actual Concentration of Regenerated Sarin in Current test kit Filtrate From Human Blood Spiked with 20 nM of Sarin

| Spiked into Blood (nM) | Correlation Factor | Estimated Actual Concentration in Current test kit Filtrate (nM) |
|---|---|---|
| 20 | 0.089 | 1.775 |
| 20 | 0.077 | 1.537 |
| 20 | 0.087 | 1.738 |
| Mean Estimate Regenerated [Sarin], nM (±STD) | | 1.68 (±0.1) |

TABLE 10

Concentration of Regenerated Sarin Recovered in Current test kit Filtrate From a 20 nM Spiked Sarin Blood Sample, as Calculated With Enzyme Inhibition Calibration Plot Provided By Current test kit Protocol

| Spiked Sarin (20 nM) Blood Samples | Amt of sarin regen (nM) | Mean | Stdev |
|---|---|---|---|
| R1 (070806) | 1.54 | 1.472 | 0.347 |
| R2 (070806) | 1.21 | | |
| R4 (080806) | 1.98 | | |
| R5 (080806) | 1.16 | | |

Ruggedisation of Laboratory-Based Microplate Reader for Field Use

Figure 26:
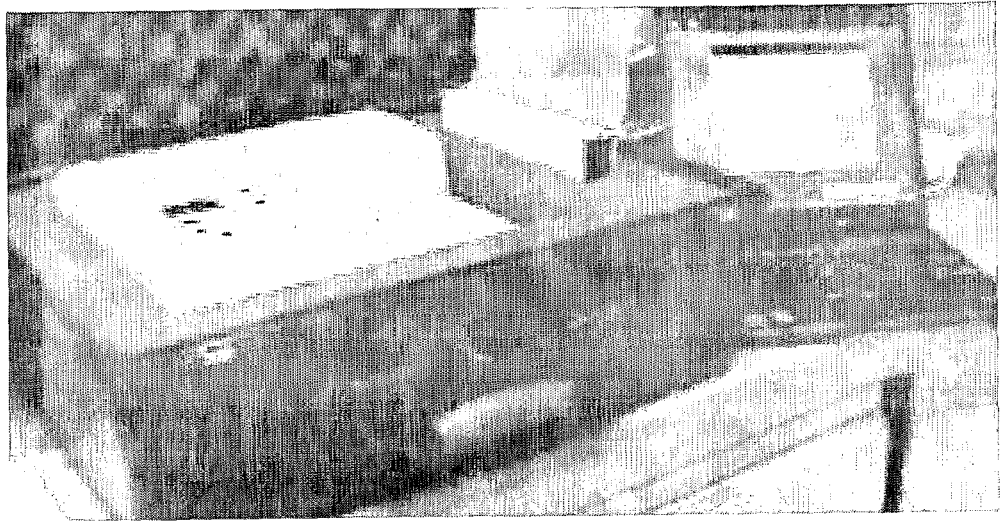
FIG. 26: An exemplary microplate reader in its transit case connected to a laptop for controlling data acquisition and interpretation of data for use in detection of cholinesterase inhibitor.
Figure 27:
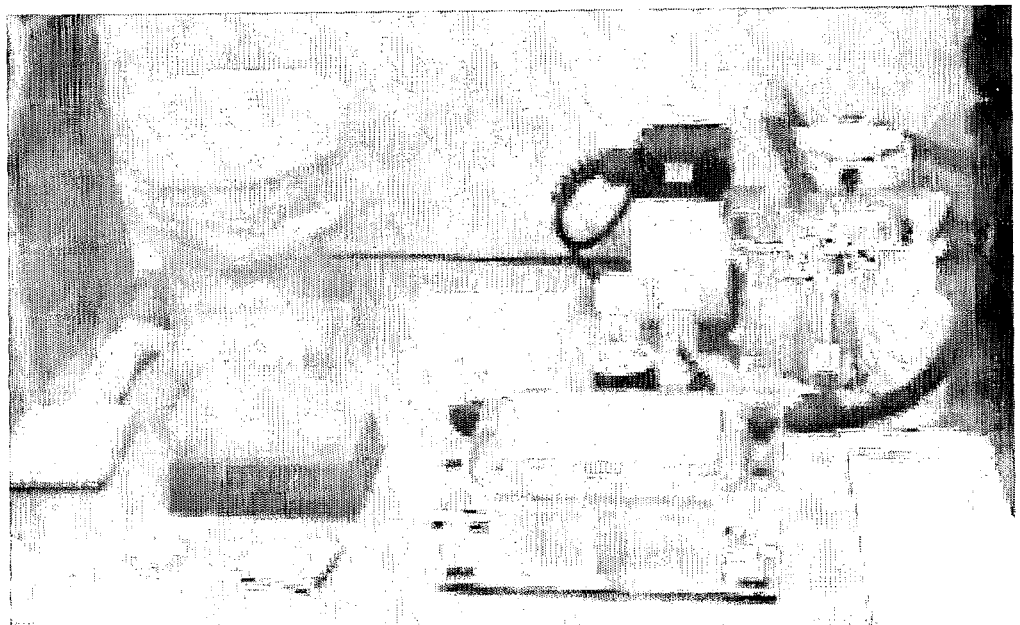
FIG. 27: An exemplary Diagnostic Kit with accessories for use in detection of cholinesterase inhibitor.

The Current test diagnostic kit comes in 2 transit cases: one for a 5.5 kg microplate reader, and the other for accessories like small vacuum pump, vacuum manifold and consumables. Both these transit cases weighed less than 13 kg each. The setup of the microplate reader with laptop is shown in FIG. 26 and the FIG. 27 showed the estimated table space requirement for performing the assay. The reader, when emplaced securely within the transit cases, was determined to be unaffected by environmental qualification tests for shock and vibration.

One important consideration for improving upon the original Current test kit kit prototype is the issue of "ruggedness". The initial Current test kit prototype has components made of glass, which made the kit fragile. Hence, for the new HTP diagnostic kit (Current test), we replaced all the glass components and selected only plastic materials for the consumables of the kit. The platform for immobilisation of AChE was glass vial in the original Current test kit prototype, whereas in the HTP version, it was replaced with 96-well plate. The technologies for immobilisation of AChE onto plastic 96-well plates, and the stabilisation of AChE after it was immobilised (thereafter called ImmAChE) remained unchanged.

Current Test Kit Reagents Preparation and Packaging Issues

Figure 28:
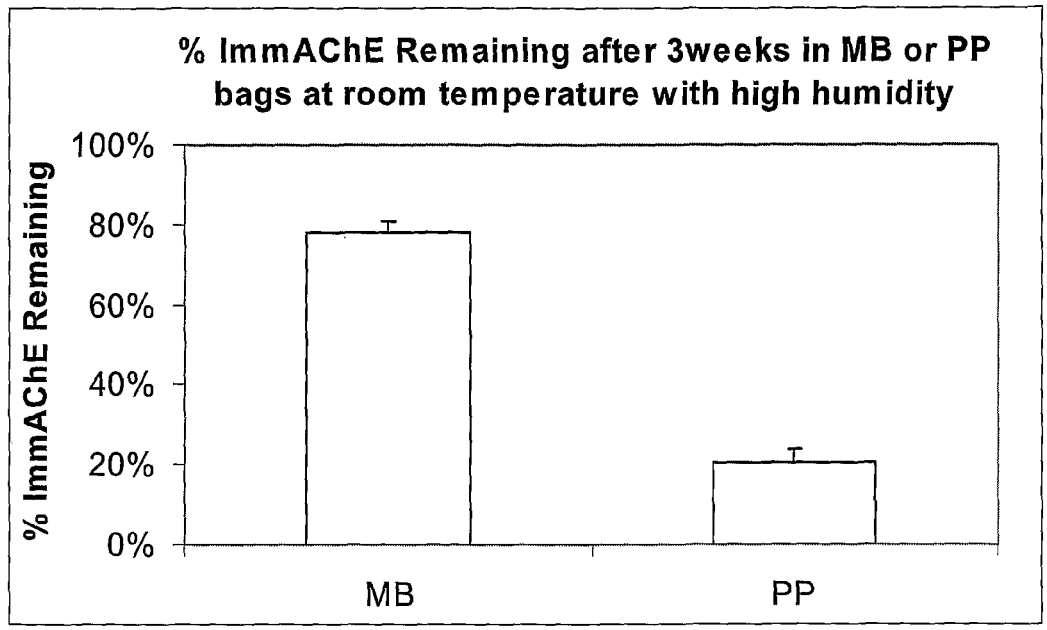
FIG. 28: Comparing the type of bags used for vacuum-sealing of immobilised cholinesterase enzyme on its stability at high humidity and ambient room temperature of 24° C.

FIG. 28 showed the importance of selecting the correct type of storage bags for our moisture-sensitive lyophilised ImmAChE. ImmAChE plates were lyophilised and stored in either PP bags or MB bags for up to 3 weeks at room temperature of about 24° C., with high humidity. ImmAChE packed in PP bags degraded much faster than the ImmAChE packed in MB bags. Hence the MB bags were really useful in protecting the ImmAChE inside from moisture. Comparing the type of bags used for vacuum-sealing of ImmAChE plates. Lyophilised ImmAChE plates were packed in either PP bags or MB bags under vacuum and stored at air-conditioned environment inside a ziplock bag sprayed with water to simulate high humidity or wetness. After 3 weeks, the plates were assayed for remaining ImmAChE activity and data were normalised to the activity prior to lyophilisation.

Normally heat-sensitive reagents like the enzyme AChE or the substrate ASChI require extreme cold storage less than −20° C. For ASChI, which is hygroscopic, light-sensitive and easily subjected to self-hydrolysis to thiocholine, we attempted to stabilise it by lyophilisation. In our investigation, both the substrate ASChI and chromogen DTNB were lyophilised together for 2 days, and tested to see if the lyophilisation procedure and storage at 45° C. for up till 8 weeks caused any change to the chemicals. The dried reagents were reconstituted with PB pH 8.0 and compared to the normal freezer stocks of ASChI and DTNB. FIG. 19 showed that there was not much difference in the lyophilised stocks of ASChI and DTNB as compared to the freezer stocks after lyophilisation and even after 8 weeks of storing the lyophilised stocks at 45° C.

Figure 29:
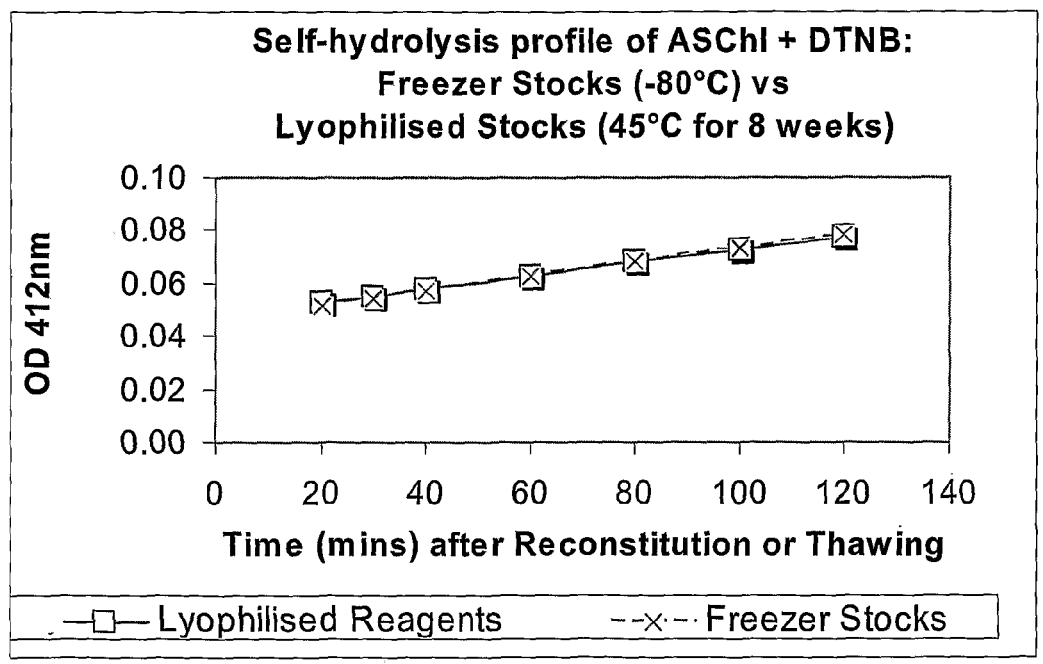
FIG. 29: Self-Hydrolysis Profiles of the substrate and concomitant reaction of the hydrolysed substrate with chromogen for substrate and chromogen package kept either in the freezer or lyophilised and vacuum-sealed.

Comparison of freezer stocks of reagents ASChI and DTNB with lyophilised stocks kept at 45° C. for 8 weeks is shown in FIG. 29. ASChI and DTNB dissolved in water and PB pH 8.0 respectively were lyophilised together for 2 days at −40° C. The dried reagents were then packed in moisture-barrier bag and kept at 45° C. for up to 8 weeks. The reagents were reconstituted with PB pH8.0, and monitored spectrophotometrically at 412 nm over time. As control, freezer stocks of the same reagents were thawed and monitored over time after thawing and dilution.

From FIG. 29, we also observed that ASChI will self-hydrolyse to thiocholine when reconstituted with PB, which will in turn react with DTNB to form yellow colour, as seen by the steady increase in optical density (OD at 412 nm) over time. The rate of self-hydrolysis of ASChI in solution upon reconstitution from lyophilised reagents was comparable to the rate observed with thawed and diluted freezer stocks. This indicated that the lyophilisation process did not affect the stability of the ASChI substrate. From this result, we recommend that the reagents provided in the test kit be used for a maximum of an hour after reconstitution with PB, and to discard all reagents thereafter.

Development of Software for Rapid and Easy Management and Interpretation of Assay Data by Paramedics FIG. 30 showed an example of the Excel sheet template, after the numeric raw data (for both Pre-Inhibition Read and Post-inhibition Read) were being pasted into the template, with the interpreted results appearing automatically as "X" for nerve agent exposure and "OK" for no exposure. The wells highlighted blue, yellow and pink represented wells incubated with filtrate from sarin-spiked blood samples corresponding to 200 nM, 100 nM and 50 nM respectively. Only wells incubated with filtrate from 200 nM and 100 nM sarin-spiked blood showed an "X", whereas wells incubated with filtrate from blood spiked with 50 nM sarin were not indicative of sarin presence, even though they caused an inhibition of about 10% of the ImmAChE wells. This was due to the fact the algorithms in this Excel template are currently based only on the non-specific inhibition of only 5 normal individuals with a large margin for error (Table 4). Hence more normal blood controls from individuals will be needed to be tested to represent a more accurate threshold value.

Within the same Excel sheet template, a record sheet was created for entry of each individual's name and NRIC number (FIG. 31). The results that appear here is linked to the 96-well format in FIG. 30 for ease of correlation of the interpreted data to each individual.

As the platform for the ImmAChE plate is bought commercially and sometimes certain wells might not immobilise AChE well, this can result in an extremely low initial value (pre-inhibition value) for those wells. Therefore it is important to determine the initial ImmAChE values for the whole plate prior to inhibition with the resultant filtrate (termed as Pre-inhibition Read), so that any inherent error due to well-to-well differences can be corrected. In this way, we could normalise each single well of Post-inhibition Read with its respective value for Pre-inhibition Read. Although this process will add another 3-5 mins to the whole procedure, it can help to minimise the occurrence of false positives.

Modifications of the above-described modes of carrying out the various embodiments of this invention will be apparent to those skilled in the art based on the above teachings related to the disclosed invention. The above embodiments of the invention are merely exemplary and should not be construed to be in any way limiting.

We claim:

1. A method of detecting an amount of a cholinesterase inhibitor in a sample comprising steps of:
   (a) contacting the sample with an agent capable of recovering the cholinesterase inhibitor from the sample so that the cholinesterase inhibitor is recovered, wherein the agent comprises a reactivity towards phosphyl moieties;
   (b) isolating the recovered cholinesterase inhibitor from the sample;
   (c) contacting the isolated cholinesterase inhibitor from step (b) with a test cholinesterase wherein the cholinesterase activity of the test cholinesterase before step (c) is known; and
   (d) measuring the cholinesterase activity to determine the amount of cholinesterase inhibitor in the sample based on the inhibition of the test cholinesterase activity from the known activity of the test cholinesterase before step (c).

2. The method of claim 1 wherein the known activity of the test cholinesterase before step (c) is a maximal cholinesterase activity independent of an individual's pre-exposure level of cholinesterase, and the method further comprises a pre-measurement step to measure the maximal cholinesterase activity of the test cholinesterase before step (c).

3. The method of claim 1 wherein proteins are removed from the sample after step (a).

4. The method of claim 3 wherein one of the proteins is cholinesterase.

5. The method of claim 3 wherein the proteins are removed by protein precipitation with a high concentration of salt.

6. The method of claim 5 wherein the salt is selected from the group consisting of citrate, phosphate, sulphate, acetate, chloride, nitrate, thiocyanate, ammonium sulphate, and combinations thereof.

7. The method of claim 5 wherein the high concentration of salt is a saturated salt.

8. The method of claim 1 wherein the sample is a biological sample.

9. The method of claim 1 wherein the agent capable of recovering a cholinesterase inhibitor from a sample comprises an active site of an oxime or fluoride ions or molybdite ions, or magnesium ions, or cobalt ions, or nickel ions, or copper salts.

10. The method of claims 1 wherein the cholinesterase is recovered in an acidic environment.

11. The method of claim 10 wherein the acidic environment comprises potassium fluoride or sodium fluoride.

12. The method of claim 10 wherein the acidic environment further comprises an acetate buffer.

13. The method of claim 3 further comprising a step of removing the agent from the sample prior to the proteins being removed.

14. The method of claim 13 wherein the agent is removed by filtration, which comprises passing the sample through a filter.

15. The method of claim 14 wherein the filter is an inert hydrophilic filter.

16. The method of claim 14 wherein the filtration comprises pumping or vacuum filtration through to a detection site.

17. The method of claim 16 wherein the filtration is facilitated with a vacuum pump set at a pressure of about 10 Hg or more for a duration of about 1 minute.

18. The method of claim 14 wherein the filter is packed with beads conjugated with aluminium, alumina, or aluminium oxide.

19. The method of claim 2 wherein the cholinesterase is washed before the pre-measurement of the maximal cholinesterase activity.

20. The method of claim 19 wherein the pre-measurement step to determine the maximal cholinesterase activity comprises a chromogenic assay mixture comprising: a substrate and a chromogen.

21. The method of 20 wherein the pre-measurement step to determine the maximal cholinesterase activity is performed at ambient temperature to 37° C. and at a pH range of 7.3 to 8.0.

22. The method of claim 20 wherein the cholinesterase activity is measured spectrophotometrically.

23. The method of claim 22 wherein the spectrophotometrical measurement is in the range of 320 to 610 nm.

24. The method of claims 22 wherein the spectrophotometrical measurement is about 412 nm where DTNB is the chromogen.

25. The method of claim 22 wherein the spectrophotometrical measurement is about 324 where PDS is the chromogen.

26. The method of claims 22 wherein the spectrophotometrical measurement is about 606 nm where 2,6-dichloroindophenol is the chromogen.

27. The method of claim 1 further comprising incubating the sample with the agent capable of recovering a cholinesterase inhibitor and/or an acetate buffer before the cholinesterase inhibitor is recovered through step (a).

28. The method of claim 27 further comprising incubating the cholinesterase inhibitor with the cholinesterase for about 1 to 20 minutes or more.

29. The method of claim 28 further comprising a washing step after the inhibition step wherein the cholinesterase inhibitor is washed with a buffer.

30. The method of claim 29 further comprising stabilizing the immobilised cholinesterase with a surfactant during the washing step.

* * * * *